United States Patent
Minomi et al.

(10) Patent No.: US 9,976,142 B2
(45) Date of Patent: May 22, 2018

(54) TARGETING MOLECULE AND A USE THEREOF

(71) Applicant: Nitto Denko Corporation, Osaka (JP)

(72) Inventors: Kenjiro Minomi, Osaka (JP);
Hirokazu Takahashi, Osaka (JP);
Erika Terada, Osaka (JP); Yoshiro Niitsu, Hokkaido (JP)

(73) Assignee: Nitto Denko Corporation, Osaka (JP)

( * ) Notice: Subject to any disclaimer, the term of this patent is extended or adjusted under 35 U.S.C. 154(b) by 0 days. days.

(21) Appl. No.: 15/301,258

(22) PCT Filed: Apr. 1, 2015

(86) PCT No.: PCT/JP2015/060353
§ 371 (c)(1),
(2) Date: Sep. 30, 2016

(87) PCT Pub. No.: WO2015/152332
PCT Pub. Date: Oct. 8, 2015

(65) Prior Publication Data
US 2017/0022500 A1    Jan. 26, 2017

(30) Foreign Application Priority Data
Apr. 2, 2014 (JP) ................ 2014-075953

(51) Int. Cl.
*A61K 38/00* (2006.01)
*C12N 15/113* (2010.01)
*A61K 9/127* (2006.01)
*A61K 31/713* (2006.01)
*A61K 38/17* (2006.01)
*A61K 47/64* (2017.01)
*C12N 15/11* (2006.01)

(52) U.S. Cl.
CPC .......... *C12N 15/113* (2013.01); *A61K 9/1271* (2013.01); *A61K 31/713* (2013.01); *A61K 38/00* (2013.01); *A61K 38/1703* (2013.01); *A61K 47/64* (2017.08); *C12N 15/111* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,966,773 A | 10/1990 | Gressel et al. | |
| 5,643,584 A | 7/1997 | Farng et al. | |
| 5,811,119 A | 9/1998 | Mehta et al. | |
| 5,851,538 A | 12/1998 | Froix et al. | |
| 6,183,774 B1 | 2/2001 | Aust et al. | |
| 8,173,170 B2 | 5/2012 | Niitsu et al. | |
| 8,178,124 B2 | 5/2012 | Niitsu et al. | |
| 8,574,623 B2 | 1/2013 | Niitsu et al. | |
| 8,652,526 B2 | 2/2014 | Niitsu et al. | |
| 8,686,052 B2 | 4/2014 | Niitsu et al. | |
| 2002/0012998 A1 | 1/2002 | Gonda et al. | |
| 2003/0096739 A1 | 5/2003 | Morris | |
| 2003/0161791 A1 | 8/2003 | Bentley et al. | |
| 2003/0211143 A1 | 11/2003 | Liu et al. | |
| 2004/0028682 A1 | 2/2004 | Border et al. | |
| 2005/0004064 A1 | 1/2005 | Tei et al. | |
| 2005/0165227 A1 | 7/2005 | Vlahov et al. | |
| 2006/0013775 A1 | 1/2006 | Gristwood et al. | |
| 2006/0074041 A1 | 4/2006 | Johnston et al. | |
| 2008/0057030 A1 | 3/2008 | Crager | |
| 2008/0279765 A1 | 11/2008 | Chettibi et al. | |
| 2009/0105179 A1 | 4/2009 | Yu et al. | |
| 2010/0028416 A1 | 2/2010 | Yu et al. | |
| 2011/0104255 A1 | 5/2011 | Niitsu et al. | |
| 2011/0178157 A1 | 7/2011 | Jin et al. | |
| 2011/0229558 A1 | 9/2011 | Niitsu et al. | |
| 2012/0269886 A1 | 10/2012 | Niitsu et al. | |

(Continued)

FOREIGN PATENT DOCUMENTS

EP    1842557    10/2007
EP    2 682 406 A2    1/2014

(Continued)

OTHER PUBLICATIONS

Choi et al. (Biochemical and Biophysical Research Communications 418 (2012) 191-197).*
Andrew, E.R., et al., "Molecular motion in solid all-trans retinoic acid (vitamin A acid) by proton NMR." Solid State Nuclear Magnetic Resonance 13, pp. 39-43, 1998.
Beljaars, L., et al. "Albumin Modified With Mannosa 6-Phosphate: A Potential Carrier for Selective Delivery of Antifibrotic Drugs to Rat and Human Hepatic Stellate Cells." Hepatology vol. 29, No. 5, pp. 1486-1493, 1999.
Blomhoff et al., "Hepatic Uptake of [H] Retinol Bound to the Serum Retinol Binding Protein Involves Both Parenchymal and Perisinusoidal Stellate Cells," The Journal of Biological Chemistry 1985; 260(25): 13571-13575.
Blomhoff, Rune, et al., Newly Administered [$^3$ H] Retinol is Transferred from Hepatocytes to Stellate Cells in Liver for Storage. Experimental Cell Research, vol. 150, pp. 186-193, 1984.

(Continued)

Primary Examiner — Jennifer Pitrak McDonald
Assistant Examiner — Sergio Coffa
(74) Attorney, Agent, or Firm — Knobbe, Martens, Olson & Bear, LLP

(57) ABSTRACT

Provided are: a targeting molecule targeting a target cell which is selected from the group consisting of a stellate cell, a myofibroblast, a cancer-associated fibroblast, a tumor cell and a cell expressing STRA6, said targeting molecule being selected from the group consisting of (1) a peptide containing an amino acid sequence in the cell-binding region of RBP, (2) a variant peptide of the aforesaid peptide (1), said variant peptide having a comparable targetability to peptide (1), and (3) a peptide mimetic having a comparable targetability to peptide (1) or peptide (2); a targeting agent, a carrier, a complex and a medicinal composition each comprising the targeting molecule; a method for treating, examining, diagnosing or monitoring a disease related to the aforesaid target cell; a method for labeling, detecting or imaging the target cell, etc.

2 Claims, 3 Drawing Sheets

(56) References Cited

U.S. PATENT DOCUMENTS

| | | |
|---|---|---|
| 2012/0328694 A1 | 12/2012 | Niitsu et al. |
| 2013/0011336 A1 | 1/2013 | Niitsu et al. |
| 2013/0045272 A1 | 2/2013 | Niitsu et al. |
| 2013/0136789 A1 | 5/2013 | Niitsu et al. |
| 2013/0171127 A1 | 7/2013 | Niitsu et al. |
| 2013/0171240 A1 | 7/2013 | Niitsu et al. |
| 2013/0172401 A1 | 7/2013 | Niitsu et al. |
| 2013/0210744 A1 | 8/2013 | Niitsu et al. |
| 2013/0216611 A1 | 8/2013 | Niitsu et al. |
| 2013/0267581 A1 | 10/2013 | Niitsu et al. |
| 2014/0127187 A1 | 5/2014 | Niitsu et al. |
| 2014/0315975 A1 | 10/2014 | Niitsu et al. |
| 2014/0323550 A1 | 10/2014 | Ayabe et al. |

FOREIGN PATENT DOCUMENTS

| | | |
|---|---|---|
| JP | H05/194278 A | 8/1993 |
| JP | H08/151335 | 6/1996 |
| JP | 08-268906 | 10/1996 |
| JP | H08/310971 A | 11/1996 |
| JP | 11-269076 | 10/1999 |
| JP | 2002-047211 | 2/2002 |
| JP | 2002-308802 A | 10/2002 |
| JP | 2002-363094 | 12/2002 |
| JP | 2002-371006 | 12/2002 |
| JP | 2003-119138 | 4/2003 |
| JP | 2003-219893 | 8/2003 |
| JP | 4121537 B2 | 7/2008 |
| JP | 5373322 B2 | 10/2009 |
| JP | 2012/501963 A | 1/2012 |
| WO | WO 1991/004748 | 4/1991 |
| WO | WO 2000/064478 | 11/2000 |
| WO | WO 2003/009881 | 2/2003 |
| WO | WO 2003/045383 | 6/2003 |
| WO | WO 2004/001381 | 12/2003 |
| WO | WO 2004/019921 | 3/2004 |
| WO | WO 2004/069159 | 8/2004 |
| WO | WO 2004/069284 | 8/2004 |
| WO | WO 2004/090108 | 10/2004 |
| WO | WO 2005/082402 | 9/2005 |
| WO | WO 2005/120587 | 12/2005 |
| WO | WO 2006/068232 | 6/2006 |
| WO | WO 2008/120815 | 9/2008 |
| WO | WO 2009/036368 | 3/2009 |
| WO | WO 2009/116257 | 9/2009 |
| WO | WO 2010/014117 | 2/2010 |
| WO | WO 2010/026766 | 3/2010 |
| WO | WO 2010/029760 | 3/2010 |
| WO | WO 2011/072082 | 6/2011 |
| WO | WO 2011/079280 A2 | 6/2011 |
| WO | WO 2011/158933 | 12/2011 |
| WO | WO 2012/044620 | 4/2012 |
| WO | WO 2012/170952 | 12/2012 |
| WO | WO 2013/073667 | 5/2013 |
| WO | WO 2013/185116 | 12/2013 |

OTHER PUBLICATIONS

Choi et al., "Recombinant fusion protein of albumin-retinol binding protein inactivates stellate cells", Biochem. Biophys. Res. Commun., 418, 191-197 (2012).

Devi, GR. "siRNA-based Approaches in Cancer Therapy", Cancer Gene Therapy (2006) 13, 819-29.

Dixon et al., "Nomenclature of Retinoids." Pure & Appl. Chem., vol. 55, No. 4, pp. 721-726 (1983).

Dunham et al., Membrane fusion: Studies with a calcium-sensitive dye, arsenazo III, in liposomes. Proceedings of the National Academy of Science, USA, vol. 74, No. 4, pp. 1580-1584, 1997.

Fallowfield, "Targeted treatments for cirrhosis", Expert Opinion. Ther. Targets, 8(5), 423-435 (2004).

Fortuna V.A. et al., "Hepatic Stellate Cells Uptake of Retinol Associated With Retinol-Binding Protein or With Bovine Serum Albumin," Journal of Cellular Biochemistry 2003; 90(4):792-805.

Friedman, S. L., "Targeting siRNA to arrest fibrosis," Nature Biotechnology (Apr. 2008) 26(4): 399-400.

Fuja et al., "Transdifferentiation of vocal-fold stellate cells and all-trans retinol-induced deactivation", Cell Tissue Res., 322(3), 417-424 (2005).

George et al., "In vivo inhibition of rat stellate cell activation by soluble transforming growth factor β type II receptor: A potential new therapy for hepatic fibrosis" Proc. Natl. Acad. Sci. USA., 96(22), 12719-12724 (1999).

Goodman et al., "Extraction and Recombination Studies of the Interaction of Retinol with Human Plasma Retinol-Binding Protein." Journal of Lipid Research, vol. 13, 1972, pp. 338-347.

Jaster, "Molecular regulation of pancreatic stellate cell function" Mol. Cancer, 3:26 (2004).

Kamps, J.Aam. et al., "Massive targeting of liposomes, surface-modified with anionized albumins, to hepatic endothelial cells," Proceedings of the National Academy of Sciences USA 1997; 94(21):11681-11685.

Kang et al., "Mannose-6-phosphateyinsulin-like growth factor-II receptor is a retinoic acid." Proc. Natl. Acad. Sci., vol. 95, pp. 13671-13676, Dec. 1998.

Kikuchi, H., Liposomes based on nanotechnology. Past, present and future. Part II, Pharm Tech Japan 2003; 19(3):419-433.

Kim et al., "Folate-tethered emulsion for the target delivery of retinoids to cancer cells." European Journal of Pharmaceutics and Biopharmaceutics. 68:618-625. (2008).

Lecchi et al., "Instrumentation and probes for molecular and cellular imaging", The Quarterly Journal of Nuclear Med.and Mol. Imaging, 51(2), 111-126 (2007).

Li, D. et al., "Liver fibrogenesis and the role of hepatic stellate cells: New insights and prospects for therapy," Journal of Gastroenterology and Hepatology 1999; 14(7):618-633.

Lim et al., "Formulation parameters determining the physicochemical characteristics of solid lipid nanoparticles loaded with all-trans retinoic acid." International Journal of Pharmaceutics. 243:135-146. (2002).

Ma et al., "Comparison of Stability for All-trans Retinoic Acid Nanosuspensions and Lipid Nanoparticle Formulations." International Conference on Complex Medical Engineering. 197-202. (2007).

Madro et al., "The role of pancreatic stellate cells and cytokines in the development of chronic pancreatitis", Med. Sci. Monit., 10(7), RA166-170 (2004).

Marcucci et al., "Active targeting with particulate drug carriers in tumor therapy: fundamentals and recent progress." Drug Discovery Today. 9(5):219-228. (2004).

Nastruzzi et al., "Liposome-associated retinoic acid increased in vitro antiproliferative effects on neoplastic cells" FEBS Letters (1990) 259(2):293-296.

Nobs et al., "Current Methods for Attaching Targeting Ligands to Liposomes and Nanoparticles", Journal of Pharmaceutical Sciences, vol. 93, No. 8, Aug. 20014.

Park et al., "Retinol Binding Protein-Albumin Domain III Fusion Protein Deactivates Hepatic Stellate Cells" Molecules and Cells, 34, 517-522 (2012).

Qi et al., "Blockade of type β transforming growth factor signaling prevents liver fibrosis and dysfunction in the rat" Proc. Natl. Acad. Sci. USA., 96(5), 2345-2349 (1999).

Reddy et al., "Contrast-enhanced endoscopic ultrasonography", World J. Gastroenterol, 17(1), 42-48 (2011).

Sato et ai, "Resolution of liver cirrhosis using vitamin A-coupled liposomes to deliver siRNA against a collagen-specific chaperone", Nature Biotechnology (2008) 26(4):431-442.

Schaefer et al., "The Synthesis of Proteoglycans in Fat-Storing Cells of Rat Liver", Hepatology, 7(4), 680-687 (1987).

Scherer et al; "Approaches for the sequence-specific knockdown of mRNA" Nature Biotechnology 2003, 21(12)1457-1465.

Selman et al., "Idiopathic Pulmonary Fibrosis: Prevailing and Evolving Hypotheses about Its Pathogenesis and Implications for Therapy", Annals of Internal Medicine, 134(2), 136-151 (2001).

Singh, et al. "Liposome encapsulated vitamin A compounds exhibit greater stability and diminished toxicity." Biophysical Chemistry, vol. 73, pp. 155-162, 1998.

(56) References Cited

OTHER PUBLICATIONS

Socaciu, et al., Different Ways to Insert Carotenoids into Liposomes Affect Structure and Dynamics of the Bilayer Differently. Biophysical Chemistry, vol. 99, pp. 1-15, 2002.

Sun et al., "The Membrane Receptor for Plasma Retinol-Binding Protein, A New Type of Cell-Surface Receptor", International Review of Cell and Molecular Biology, vol. 288, pp. 1-41 (2011).

Torchilin et al., "Immunomicelles: Targeted pharmaceutical carriers for poorly soluble drugs." PNAS. 100(10):6039-6044. (2003).

Torchilin, "Recent Advances with Liposomes as Pharmaceutical Carriers", Nature Reviews, Drug Discovery., vol. 4 Feb. 2005, pp. 145-160.

Torchilin, V. P. "Drug Targeting," European Journal of Pharmaceutical Sciences. (2000) 11(2):81-91.

Torchilin, VP., "Targeted pharmaceutical nanocarriers for cancer therapy and imaging" The AAPS Journal (2007) 9(2):E128-47.

Tsuji, H. et al., "Targeting of liposomes surface-modified with glycyrrhizin to the liver. I. Preparation and biological disposition," Chemical & Pharmaceutical Bulletin 1991; 39(4):1004-08.

Vogel et al., "An immortalized rat liver stellate cell line (HSC-TS): a new cell model for the study of retinoid metabolism in vitro." Journal of Lipid Research, vol. 41, 2000, pp. 882-893.

Wassall, S.R., et al. "Retinoid-Phospholipid Interactions as Studied by Magnetic Resonance" Bulletin of Magnetic Resonance, vol. 9 No. 3, pp. 85-89, 1987.

Watanabe, et al., Treatment of idiopathic myelofiosis employing siRNA for heat shock protein 7 (siRNA/HSP47) encapsulated in liposomes, Blood (2007) 110:235.

Whitmer et al., Membrane-membrane interactions associated with rapid transfer of liposomal bilirubin to microsomal UDP-glucuronyltransferase. Biochemical Journal, vol. 244, pp. 41-47, 1987.

Wu, J. et al., "Modification of liposomes for liver targeting," Journal of Hepatology (1996)24(6):757-763.

Zhang et al., "Cationic lipids and polymers mediated vectors for delivery of siRNA," J. Control Release (2007) 123: 1-10.

Zhao et al.; "Tumor-selective targeted delivery of genes and antisense oligodeoxyribonucleotides via the folate receptor," Advanced Drug Delivery Reviews (2004) 56: 1193-1204.

Heller, Joram, "Interactions of Plasma Retinol-binding Protein with Its Receptor," The Journal of Biological Chemistry (1975), vol. 250, No. 10, pp. 3613-3619.

Kuwaguchi, et al., "A Membrane Receptor for Retinol Binding Protein Mediates Cellular Uptake of Vitamin A," Science (2007), vol. 315, pp. 820-825.

Newcomer, et al., "The three-dimensional structure of retinol-binding protein," The EMBO Journal (1984), vol. 3, No. 7, pp. 1451-1454.

Extended European Search Report dated Oct. 6, 2017 for European Application No. 15773773.5.

* cited by examiner

[Drawings]
[Fig.1]
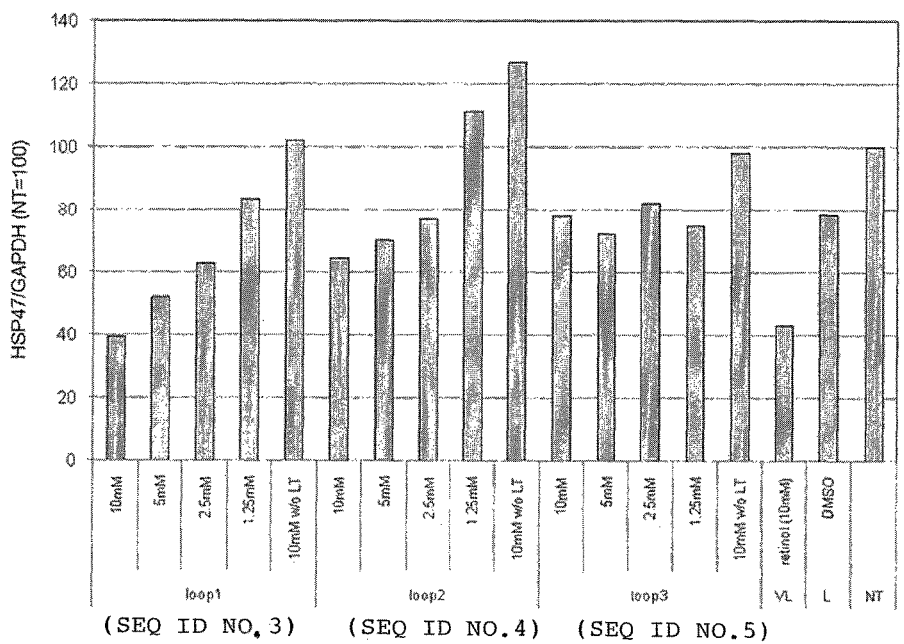
[Fig.2]
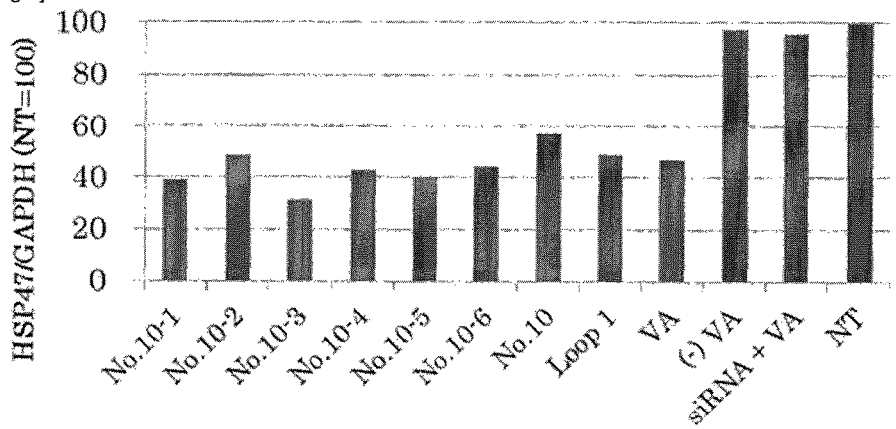

[Fig.3]
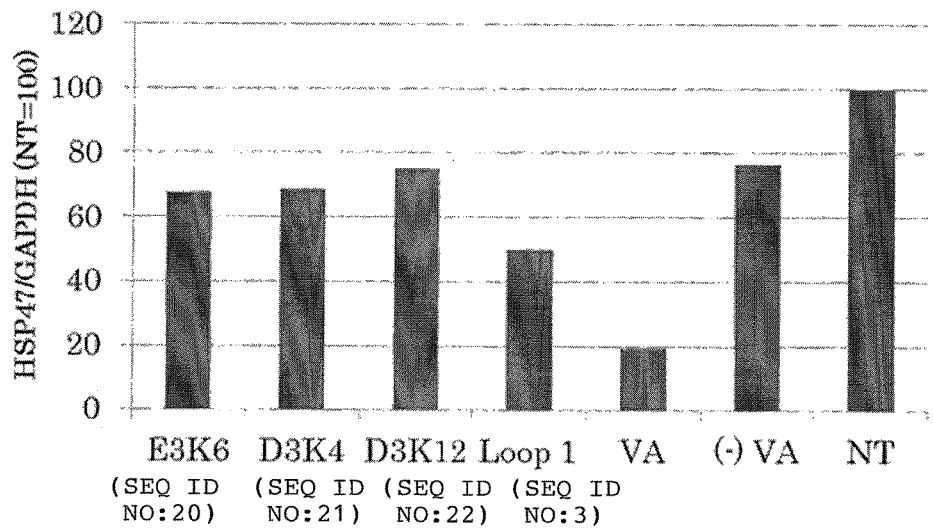
[Fig.4]
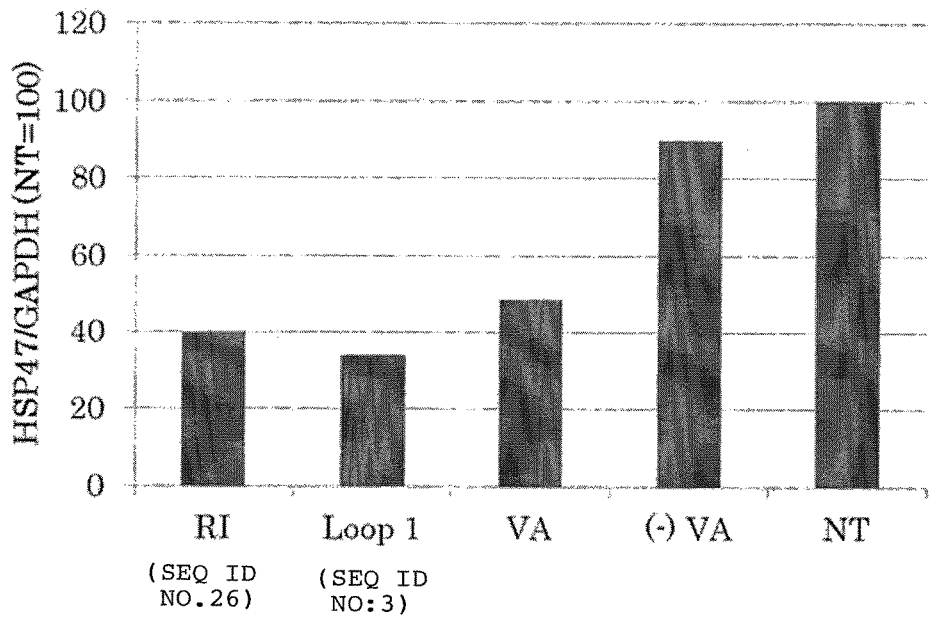

[Fig.5]
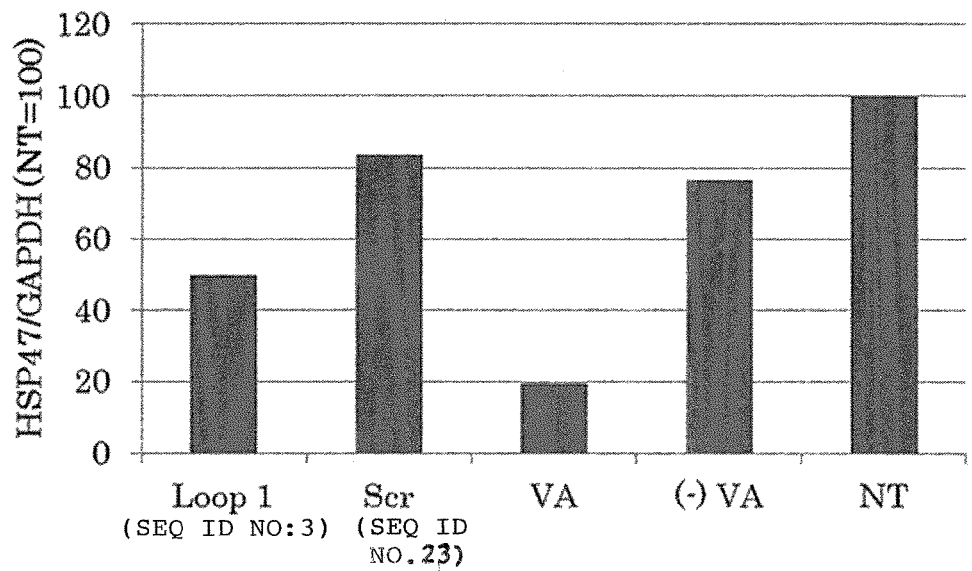
[Fig.6]
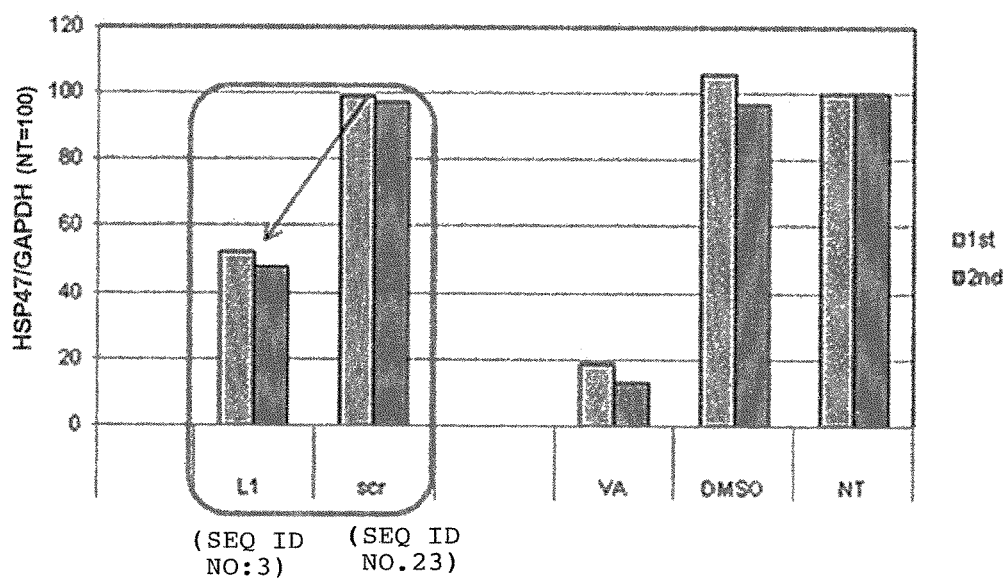

SEQUENCE LISTING

```
<160> NUMBER OF SEQ ID NOS: 26

<210> SEQ ID NO 1
<211> LENGTH: 941
<212> TYPE: DNA
<213> ORGANISM: Homo sapiens

<400> SEQUENCE: 1
cgcctccctc gctccacgcg cgcccggact cggcggccag gcttgcgcgc ggttcccctc        60
ccggtgggcg gattcctggg caagatgaag tgggtgtggg cgctcttgct gttggcggcg       120
ctgggcagcg gccgcgcgga gcgcgactgc cgagtgagca gcttccgagt caaggagaac       180
ttcgacaagg ctcgcttctc tgggacctgg tacgccatgg ccaagaagga ccccgagggc       240
ctctttctgc aggacaacat cgtcgcggag ttctccgtgg acgagaccgg ccagatgagc       300
gccacagcca agggccgagt ccgtcttttg aataactggg acgtgtgcgc agacatggtg       360
ggcaccttca cagacaccga ggaccctgcc aagttcaaga tgaagtactg gggcgtagcc       420
tcctttctcc agaaaggaaa tgatgaccac tggatcgtcg acacagacta cgacacgtat       480
gccgtgcagt actcctgccg cctcctgaac ctcgatggca cctgtgctga cagctactcc       540
```

```
ttcgtgtttt cccgggaccc caacggcctg cccccagaag cgcagaagat tgtaaggcag    600
cggcaggagg agctgtgcct ggccaggcag tacaggctga tcgtccacaa cggttactgc    660
gatggcagat cagaaagaaa ccttttgtag caatatcaag aatctagttt catctgagaa    720
cttctgatta gctctcagtc ttcagctcta tttatcttag gagtttaatt tgcccttctc    780
tccccatctt ccctcagttc ccataaaacc ttcattacac ataaagatac acgtgggggt    840
cagtgaatct gcttgccttt cctgaaagtt tctggggctt aagattccag actctgattc    900
attaaactat agtcacccgt gtcctgtgaa aaaaaaaaa a                         941
```

<210> SEQ ID NO 2
<211> LENGTH: 200
<212> TYPE: PRT
<213> ORGANISM: Homo sapiens

<400> SEQUENCE: 2

Met Lys Trp Val Trp Ala Leu Leu Leu Ala Ala Leu Gly Ser Gly
1               5                   10                  15

Arg Ala Glu Arg Asp Cys Arg Val Ser Ser Phe Arg Val Lys Glu Asn
                20                  25                  30

Phe Asp Lys Ala Arg Phe Ser Gly Thr Trp Tyr Ala Met Ala Lys Lys
            35                  40                  45

Asp Pro Glu Gly Leu Phe Leu Gln Asp Asn Ile Val Ala Glu Phe Ser
        50                  55                  60

Val Asp Glu Thr Gly Gln Met Ser Ala Thr Ala Lys Gly Arg Val Arg
65                  70                  75                  80

Leu Leu Asn Asn Trp Asp Val Cys Ala Asp Met Val Gly Thr Phe Thr
                85                  90                  95

Asp Thr Glu Asp Pro Ala Lys Phe Lys Met Lys Tyr Trp Gly Val Ala
            100                 105                 110

Ser Phe Leu Gln Lys Gly Asn Asp Asp His Trp Ile Val Asp Thr Asp
        115                 120                 125

Tyr Asp Thr Tyr Ala Val Gln Tyr Ser Cys Arg Leu Leu Asn Leu Asp
    130                 135                 140

Gly Thr Cys Ala Asp Ser Tyr Ser Phe Val Phe Ser Arg Asp Pro Asn
145                 150                 155                 160

Gly Leu Pro Pro Glu Ala Gln Lys Ile Val Arg Gln Arg Gln Glu Glu
                165                 170                 175

Leu Cys Leu Ala Arg Gln Tyr Arg Leu Ile Val His Asn Gly Tyr Cys
            180                 185                 190

Asp Gly Arg Ser Glu Arg Asn Leu
        195                 200

<210> SEQ ID NO 3
<211> LENGTH: 14
<212> TYPE: PRT
<213> ORGANISM: Artificial Sequence
<220> FEATURE:
<223> OTHER INFORMATION: Synthetic RBP loop 1

<400> SEQUENCE: 3

Ala Lys Lys Asp Pro Glu Gly Leu Phe Leu Gln Asp Asn Ile
1               5                   10

<210> SEQ ID NO 4
<211> LENGTH: 15
<212> TYPE: PRT

<213> ORGANISM: Artificial Sequence
<220> FEATURE:
<223> OTHER INFORMATION: Synthetic RBP loop 2

<400> SEQUENCE: 4

Ala Lys Gly Arg Val Arg Leu Leu Asn Asn Trp Asp Val Cys Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic RBP loop 3

<400> SEQUENCE: 5

Lys Tyr Trp Gly Val Ala Ser Phe Leu Gln Lys Gly Asn Asp Asp
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: Peptide No. 10

<400> SEQUENCE: 6

Lys Asp Pro Glu Gly Leu Phe Leu Gln Asp
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Peptide No. 10-1

<400> SEQUENCE: 7

Ala Lys Lys Asp Pro Glu Gly Leu Phe Leu Gln Asp Asn
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Peptide No. 10-2

<400> SEQUENCE: 8

Ala Lys Lys Asp Pro Glu Gly Leu Phe Leu Gln Asp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Peptide No. 10-3

<400> SEQUENCE: 9

Lys Lys Asp Pro Glu Gly Leu Phe Leu Gln Asp Asn Ile
1               5                   10

<210> SEQ ID NO 10
<211> LENGTH: 12
<212> TYPE: PRT
<213> ORGANISM: Artificial Sequence

```
<220> FEATURE:
<223> OTHER INFORMATION: Peptide No. 10-4

<400> SEQUENCE: 10

Lys Asp Pro Glu Gly Leu Phe Leu Gln Asp Asn Ile
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: Peptide No. 10-5

<400> SEQUENCE: 11

Lys Lys Asp Pro Glu Gly Leu Phe Leu Gln Asp
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: Peptide No. 10-6

<400> SEQUENCE: 12

Lys Asp Pro Glu Gly Leu Phe Leu Gln Asp Asn
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Peptide No. 10-7

<400> SEQUENCE: 13

Lys Lys Asp Pro Glu Gly Leu Phe Leu Gln Asp Asn
 1               5                  10

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule: HSP47
      siRNA sense strand

<400> SEQUENCE: 14
ggacaggccu cuacaacuat t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule: HSP47
      siRNA antisense strand

<400> SEQUENCE: 15
uaguuguaga ggccugucct t                                              21

<210> SEQ ID NO 16
<211> LENGTH: 20
<212> TYPE: DNA
<213> ORGANISM: Artificial Sequence
<220> FEATURE:
```

<223> OTHER INFORMATION: rat HSP47 forward primer

<400> SEQUENCE: 16
tgacctgcag aaacatctgg                                                      20

<210> SEQ ID NO 17
<211> LENGTH: 20
<212> TYPE: DNA
<213> ORGANISM: Artificial Sequence
<220> FEATURE:
<223> OTHER INFORMATION: rat HSP47 reverse primer

<400> SEQUENCE: 17
aggaagatga aggggtggtc                                                      20

<210> SEQ ID NO 18
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 18
accatcttcc aggagcgaga                                                      20

<210> SEQ ID NO 19
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 19
gcatggactg tggtcatgag                                                      20

<210> SEQ ID NO 20
<211> LENGTH: 14
<212> TYPE: PRT
<213> ORGANISM: Artificial Sequence
<220> FEATURE:
<223> OTHER INFORMATION: Variant peptide E3K6

<400> SEQUENCE: 20

Ala Lys Glu Asp Pro Lys Gly Leu Phe Leu Gln Asp Asn Ile
 1               5                  10

<210> SEQ ID NO 21
<211> LENGTH: 14
<212> TYPE: PRT
<213> ORGANISM: Artificial Sequence
<220> FEATURE:
<223> OTHER INFORMATION: Variant peptide D3K4

<400> SEQUENCE: 21

Ala Lys Asp Lys Pro Glu Gly Leu Phe Leu Gln Asp Asn Ile
 1               5                  10

<210> SEQ ID NO 22
<211> LENGTH: 14
<212> TYPE: PRT
<213> ORGANISM: Artificial Sequence
<220> FEATURE:
<223> OTHER INFORMATION: Variant peptide D3K12

<400> SEQUENCE: 22

Ala Lys Asp Asp Pro Glu Gly Leu Phe Leu Gln Lys Asn Ile

```
<210> SEQ ID NO 23
<211> LENGTH: 14
<212> TYPE: PRT
<213> ORGANISM: Artificial Sequence
<220> FEATURE:
<223> OTHER INFORMATION: Scramble peptide

<400> SEQUENCE: 23

Ala Lys Phe Gln Lys Leu Glu Pro Gly Asp Asp Leu Asn Ile
 1               5                   10

<210> SEQ ID NO 24
<211> LENGTH: 20
<212> TYPE: DNA
<213> ORGANISM: Artificial Sequence
<220> FEATURE:
<223> OTHER INFORMATION: human HSP47 forward primer

<400> SEQUENCE: 24
tgacctgcag aaacacctgg                                               20

<210> SEQ ID NO 25
<211> LENGTH: 20
<212> TYPE: DNA
<213> ORGANISM: Artificial Sequence
<220> FEATURE:
<223> OTHER INFORMATION: human HSP47 reverse primer

<400> SEQUENCE: 25
aggaagatga aggggtggtc                                               20

<210> SEQ ID NO 26
<211> LENGTH: 14
<212> TYPE: PRT
<213> ORGANISM: Artificial Sequence
<220> FEATURE:
<223> OTHER INFORMATION: Retro-inverso peptide (RI) of RBP Loop 1

<400> SEQUENCE: 26

Ile Asn Asp Gln Leu Phe Leu Gly Glu Pro Asp Lys Lys Ala
 1               5                   10
```

TARGETING MOLECULE AND A USE THEREOF

FIELD OF ART

The present invention relates to a targeting molecule which is targeted to a target cell selected from the group consisting of a stellate cell, a myofibroblast, a cancer-associated fibroblast, a tumor cell and an STRA6-expressing cell, a targeting agent, a carrier, a complex and a pharmaceutical composition comprising the targeting molecule, a method of treating, examining, diagnosing or monitoring a disease associated with said cell, and a method of labeling, detecting or imaging said cell, and the like.

The present application is filed with a Sequence Listing in Electronic format. The Sequence Listing is provided as a file entitled KUZU1-029APC-SUBSTITUTE.TXT, created Sep. 20, 2017, which is approximately 12 kb in size. The information in the electronic format of the sequence listing is incorporated herein by reference in its entirety.

BACKGROUND ART

Human has overcome a number of diseases by chemotherapy. However, chemotherapy using conventional small molecule drugs has been afflicted with the side effects caused by the drug acting on cells other than the target cell of the therapy. In recent years, in order to overcome this adverse effect, techniques for delivering a drug to a desired cell have been developed.

One method of delivering a drug to a desired cell is the utilization of a targeting molecule specific to the cell. For instance, retinoid and its derivative are known to function as targeting molecules specific to stellate cells, extracellular matrix-producing cells in lung, bone marrow, kidney and intestinal tracts, cancer-associated fibroblasts, and cancer cells (Patent Literatures 1-9, Non-Patent Literature 1). However, there still is a need for further targeting molecules.

PRIOR ART REFERENCES

Patent Literatures

Patent Literature 1: WO 2006/068232
Patent Literature 2: WO 2008/120815
Patent Literature 3: WO 2009/036368
Patent Literature 4: WO 2009/116257
Patent Literature 5: WO 2010/014117
Patent Literature 6: WO 2010/026766
Patent Literature 7: WO 2010/029760
Patent Literature 8: WO 2011/158933
Patent Literature 9: WO 2013/073667

Non-Patent Literature

Non-Patent Literature 1: Sato et al., Nat Biotechnol. 2008; 26(4):431-42

SUMMARY OF INVENTION

Problems to be Solved by the Invention

The present invention is aimed for providing a targeting molecule which is targeted to a target cell selected from the group consisting of a stellate cell, a myofibroblast, a cancer-associated fibroblast, a tumor cell and an STRA6-expressing cell, a targeting agent, a carrier, a complex and a composition comprising the targeting molecule, a method of treating a disease associated with said cell, and a method of labeling said cell, and the like.

Means for Solving the Problems

The inventors continued an earnest research to solve the problems described above and found that a peptide and the like comprising an amino acid sequence of the cell-binding region of RBP functions as a targeting molecule specific to the stellate cell and the like, thus completed the invention.

Accordingly, the present invention relates to the followings:

<1> A targeting molecule which is targeted to a target cell selected from the group consisting of a stellate cell, a myofibroblast, a cancer-associated fibroblast, a tumor cell and an STRA6-expressing cell, wherein the targeting molecule is selected from the group consisting of:

(1) a peptide comprising an amino acid sequence of the cell-binding region of RBP, (2) a mutant peptide of the peptide of (1) having an equal targetability as said peptide, and (3) a peptide mimetic having an equal targetability as the peptide of (1) or (2).

<2> The targeting molecule according to <1> above, wherein the cell-binding region is selected from the group consisting of Loop 1, Loop 2, and a functional fragment of Loop 1 or Loop 2 of RBP.

<3> The targeting molecule according to <1> or <2> above, wherein the cell-binding region comprises an amino acid sequence selected from SEQ ID NOS: 3 and 4.

<4> The targeting molecule according to any one of <1> to <3> above, wherein the targeting molecule comprises an amino acid sequence selected from SEQ ID NOS: 3, 4, and 6-13.

<5> The targeting molecule according to any one of <1> to <4> above, wherein the peptide mimetic is a retro-inverso peptide based on the peptide of (1) or (2).

<6> A targeting agent comprising the targeting molecule according to any one of <1> to <5> above for targeting a target cell selected from the group consisting of a stellate cell, a myofibroblast, a cancer-associated fibroblast, a tumor cell and an STRA6-expressing cell.

<7> A carrier that is targeted by the targeting molecule according to any one of <1> to <5> above and delivers a substance to a target cell selected from the group consisting of a stellate cell, a myofibroblast, a cancer-associated fibroblast, a tumor cell and an STRA6-expressing cell.

<8> A complex represented by a formula:

$$X—Y—Z \qquad (1)$$

wherein,

X is a targeting moiety comprising the targeting molecule according to any one of <1> to <5> above, Y is a binding moiety, and Z is a functional moiety comprising a substance selected from the group consisting of a drug, a label and a carrier.

<9> The complex according to <8> above, wherein the carrier further comprises a drug and/or a label.

<10> A composition comprising a component selected from the group consisting of the targeting molecule according to any one of <1> to <5> above, the targeting agent according to <6> above, the carrier according to <7>, and the complex according to <8> or <9> above.

<11> The composition according to <10> above, wherein the composition comprises a drug that treats a disease associated with a target cell selected from the group consisting of a stellate cell, a myofibroblast, a cancer-associated fibroblast, a tumor cell and an STRA6-expressing cell, and wherein the composition is for treating the disease.

<12> The composition according to <11> above, wherein the disease is selected from the group consisting of fibrosis and neoplastic diseases.

<13> The composition according to <10> above, wherein the composition comprises a drug that controls the activity or proliferation of a target cell selected from the group consisting of a stellate cell, a myofibroblast, a cancer-associated fibroblast, a tumor cell and an STRA6-expressing cell, and wherein the composition is for controlling the activity or proliferation of said target cell.

<14> The composition according to <10> above, wherein the composition is for delivering a substance to a target cell selected from the group consisting of a stellate cell, a myofibroblast, a cancer-associated fibroblast, a tumor cell and an STRA6-expressing cell.

<15> The composition according to <10> above, wherein the composition comprises a label, and wherein the composition is for labeling, detecting or imaging a target cell selected from the group consisting of a stellate cell, a myofibroblast, a cancer-associated fibroblast, a tumor cell and an STRA6-expressing cell.

<16> The composition according to <10> above, wherein the composition comprises a label, and wherein the composition is for examining, diagnosing or monitoring a disease associated with a target cell selected from the group consisting of a stellate cell, a myofibroblast, a cancer-associated fibroblast, a tumor cell and an STRA6-expressing cell.

<17> A method of treating a disease associated with a target cell selected from the group consisting of a stellate cell, a myofibroblast, a cancer-associated fibroblast, a tumor cell and an STRA6-expressing cell, wherein the method comprises a step of administrating an effective amount of the complex according to <8> or <9> above or the composition according to <11> or <12> above comprising a drug that treats the disease to a subject in need thereof.

<18> A method of labeling, detecting or imaging a target cell selected from the group consisting of a stellate cell, a myofibroblast, a cancer-associated fibroblast, a tumor cell and an STRA6-expressing cell or a tissue comprising the same, wherein the method comprises a step of administrating an effective amount of the complex according to <8> or <9> above or the composition according to <15> above comprising a label to a subject in need thereof.

<19> A method of examining, diagnosing or monitoring a disease associated with a target cell selected from the group consisting of a stellate cell, a myofibroblast, a cancer-associated fibroblast, a tumor cell and an STRA6-expressing cell, wherein the method comprises a step of administrating an effective amount of the complex according to <8> or <9> above or the composition according to <16> above comprising a label to a subject in need thereof.

Effects of the Invention

The present invention enables utilizing a peptide having an excellent workability as a targeting molecule, increasing the degree of freedom in designing a formulation, and enabling the development of more diverse targeting formulations. The present invention also enables specifically delivering various drugs to causal cells of intractable disease such as fibrosis and tumor, and thereby being expected to provide a great contribution to medicine and veterinary medicine.

BRIEF DESCRIPTION OF THE DRAWINGS

FIG. 1 is a graph showing the siRNA transfection efficiency in rat hepatic stellate cells (HSCs) using RBP Loops 1-3 (SEQ ID NOs: 3-5) as the targeting molecules, as indicated by the degree of suppression of rat HSP47, the target gene of the siRNA. SEQ ID NOs: 3-5 correspond to amino acid residues 46-59, 75-89 and 107-121, respectively, of the amino acid sequence SEQ ID NO: 2. The vertical axis indicates the expression level of rat HSP47 relative to the internal standard, rat GAPDH, referring to the expression level in untreated cell as 100. In the graph, "VL" means the group using retinol instead of either loop of RBP (i.e., VA/LipoTrust/siRNA), "L" means the group using DMSO instead of either loop of RBP (i.e., LipoTrust/siRNA), "w/o LT" means the group using the mixture of siRNA and a peptide which does not comprise LipoTrust™ SR, and "NT" means the untreated group, respectively.

FIG. 2 is a graph showing the siRNA transfection efficiency in rat hepatic stellate cells (HSCs) using RBP Loop 1 (SEQ ID NO: 3) or its fragment as the targeting molecule, as indicated by the degree of suppression of rat HSP47, the target gene of the siRNA. SEQ ID NOs: 6-12 correspond to amino acid residues 3-12, 1-13, 1-12, 2-14, 3-14, 2-12, and 3-13, respectively, of the amino acid sequence SEQ ID NO: 3. The vertical axis indicates the expression level of rat HSP47 relative to the internal standard, rat GAPDH, referring to the expression level in untreated cell as 100. In the graph, "VA" means the group using retinol instead of either peptide (i.e., VA/LipoTrust/siRNA), "(-)VA" means the group using DMSO instead of either peptide (i.e., LipoTrust/siRNA), "siRNA+VA" means the group using the mixture of retinol and siRNA which does not comprise LipoTrust™ SR, and "NT" means the untreated group, respectively.

FIG. 3 is a graph showing the siRNA transfection efficiency in rat hepatic stellate cells (HSCs) using RBP Loop 1 (L1) (SEQ ID NO: 3) or its mutant peptide (E3K6 (SEQ ID NO: 20), D3K4 (SEQ ID NO: 21), D3K12 (SEQ ID NO: 22)) as the targeting molecule, as indicated by the degree of suppression of rat HSP47, the target gene of the siRNA. The vertical axis indicates the expression level of rat HSP47 relative to the internal standard, rat GAPDH, referring to the expression level in untreated cell as 100. In the graph, "VA" means the group using retinol instead of either peptide (i.e., VA/LipoTrust/siRNA), "(-)VA" means the group using DMSO instead of either peptide (i.e., LipoTrust/siRNA), and "NT" means the untreated group, respectively.

FIG. 4 is a graph showing the siRNA transfection efficiency in rat hepatic stellate cells (HSCs) using RBP Loop 1 (L1) (SEQ ID NO: 3) or its retro-inverso peptide (RI) (SEQ ID NO: 26) as the targeting molecule, as indicated by the degree of suppression of rat HSP47, the target gene of the siRNA. The vertical axis indicates the expression level of rat HSP47 relative to the internal standard, rat GAPDH, referring to the expression level in untreated cell as 100. In the graph, "VA" means the group using retinol instead of either peptide (i.e., VA/LipoTrust/siRNA), "(-)VA" means the group using DMSO instead of either peptide (i.e., LipoTrust/siRNA), and "NT" means the untreated group, respectively.

FIG. 5 is a graph showing the siRNA transfection efficiency in rat stellate cells (HSCs) using RBP Loop 1 (L1) (SEQ ID NO: 3) or its scrambled peptide as the targeting molecule, as indicated by the degree of suppression of rat HSP47, the target gene of the siRNA. The vertical axis indicates the expression level of rat HSP47 relative to the internal standard, rat GAPDH, referring to the expression level in untreated cell as 100. In the graph, "scr" means the group using the scrambled peptide (SEQ ID NO: 23), "VA" means the group using retinol instead of either peptide (i.e., VA/LipoTrust/siRNA), "DMSO" means the group using DMSO instead of either peptide (i.e., LipoTrust/siRNA), and "NT" means the untreated group, respectively.

FIG. 6 is a graph showing the siRNA transfection efficiency in human fibrosarcoma cell strain HT-1080 using RBP Loop 1 (L1) (SEQ ID NO: 3) as the targeting molecule, as indicated by the degree of suppression of human HSP47 which is the target gene of the siRNA. The vertical axis indicates the expression level of human HSP47 relative to the internal standard human GAPDH, referring to the expression level in untreated cell as 100. In the graph, "scr" means the group using the scrambled peptide (SEQ ID NO: 23), "VA" means the group using retinol instead of either peptide (i.e., VA/LipoTrust/siRNA), "DMSO" means the group using DMSO instead of either peptide (i.e., LipoTrust/siRNA), "NT" means the untreated group, and "1st" and "2nd" mean the results of the first and second experiment of the same content, respectively.

MODES FOR CARRYING OUT THE INVENTION

Unless being otherwise defined herein, all technical and scientific terms used herein have the same meanings as being usually understood by a person skilled in the art. All patents, patent applications, published patent applications and other publications (including on-line information) are incorporated herein in its entity by reference.

An aspect of the present invention relates to a targeting molecule which is targeted to a target cell selected from the group consisting of a stellate cell, a myofibroblast, a cancer-associated fibroblast, a tumor cell and an STRA6-expressing cell, wherein the targeting molecule is selected from the group consisting of:

(1) a peptide comprising an amino acid sequence of the cell-binding region of RBP, (2) a mutant peptide of the peptide of (1) having an equal targetability as the peptide of (1), (3) a peptide mimetic having an equal targetability as the peptide of (1) or (2).

A "targeting molecule" herein means a molecule having a targetability to promote the delivery of a substance bound to the molecule to a specific target. In the present invention, the target is a cell selected from the group consisting of a stellate cell, a myofibroblast, a cancer-associated fibroblast, a tumor cell and an STRA6-expressing cell, and the targeting molecule of the present invention has an ability to promote the delivery of a substance bound thereto to these target cells, i.e., a targetability. Here, "to promote the delivery" means delivering a substance to the target cell quickly and/or in a large amount, and/or allowing the substance being taken up, as compared to the case without the targeting molecule. This can easily be confirmed, for instance, by adding a targeting molecule with a label or a drug attached thereto or a targeting molecule bound to a composition comprising a label or a drug to a culture of the target cell and comparing the localization of the label or the action of the drug after a defined time to those in the presence of the label or the drug which is not bound to the targeting molecule (see, e.g., Examples 2-6 in the present specification). The delivery is considered to be promoted if the level of the label or the effect of the drug is increased in the presence of the targeting molecule as compared to those in the absence of the targeting molecule. The degree of the increase may be, without being limited, such as, for example, 5% or more, 10% or more, 15% or more, 20% or more, 25% or more, 30% or more, 40% or more, 50% or more, 60% or more, 70% or more, 80% or more, 90% or more, 100% or more, 150% or more, 200% or more, or 300% or more. It is preferred that the level of the label or the action of the drug in the target cell in the presence of the targeting molecule is increased with statistical significance as compared with the case in the absence of the targeting molecule.

A "stellate cell" herein typically refers to a star-formed cell having an ability to store vitamin A (VA). For this characteristic, "stellate cell" is sometimes called a "vitamin A storage cell". As a stellate cell, the hepatic stellate cell (Ito cell) in liver is well known. However, it has been known there are similar cells other than in liver, for example, in pancreas and vocal cord (see, e.g., Madro et al., Med Sci Monit. 2004 July; 10(7):RA166-70, Jaster, Mol Cancer. 2004 Oct. 6; 3(1):26, Fuja et al., Cell Tissue Res. 2005; 322(3):417-24), and the stellate cell in the present invention encompasses these cells. A stellate cell is known to exhibit a myofibroblast-like phenotype which is characterized in the expression of α-smooth muscle actin (αSMA) upon being activated by a stimulation such as inflammation, and proliferate and produce a large amount of collagen, which can be a cause of fibrosis (see, e.g., Fallowfield and Iredale, Expert Opin Ther Targets. 2004 October; 8(5):423-35, Madro et al., 2004, supla, Jaster, 2004, supla). The stellate cell in the present invention encompasses both inactivated stationary (quiescent) stellate cell and activated stellate cell.

A "myofibroblast" herein refers to a fibroblast characterized in the expression of αSMA, and it appears in various organs. A myofibroblast differentiates from a mesenchymal cell such as fibroblast present in various organs and in circulating blood and are considered to be involved in fibrosis and regeneration of various organs (see, e.g., Selman et al., Ann Intern Med. 2001 Jan. 16; 134(2):136-51). A myofibroblast can be identified by immunostaining using a detectably labeled anti-α-SMA antibody, etc.

A "cancer-associated fibroblast (CAF)" herein means the α-SMA (smooth muscle actin)-positive fibroblast present inside and/or around a cancer lesion (see, e.g., Patent Literature 2). CAF is considered to assist the proliferation of cancer cells present nearby and to be involved in the progression of cancer, etc. CAF can be identified by immunostaining of cancer tissue or cells isolated from cancer tissue with a detectably labeled anti-α-SMA antibody.

The presence of CAF has been identified in various cancers such as colorectal cancer, lung cancer, prostate cancer, breast cancer, gastric cancer, bile duct cancer and basal cell cancer. According to the present invention, whether a cell is CAF or not is determined by the following technique. Namely, cells that are present inside and/or around a cancer lesion is immunostained with a labeled antibody for a CAF marker, α-SMA, such as, for example, a FITC-labeled anti-α-SMA antibody or a Cy3-labeled anti-α-SMA antibody, and those in which α-SMA is detected are determined to be CAF.

The cancer associated with CAF in the present invention is not particularly limited and includes, for example, solid tumors such as brain tumor, head and neck cancer, breast cancer, lung cancer, esophageal cancer, gastric cancer, duodenal cancer, appendiceal cancer, colorectal cancer, rectal cancer, hepatic cancer, pancreatic cancer, gallbladder cancer, bile duct cancer, anal cancer, renal cancer, ureteral cancer, bladder cancer, prostate cancer, penile cancer, testicular cancer, uterine cancer, ovarian cancer, vulvar cancer, vaginal cancer and skin cancer. Although CAF is typically associated with a cancer, it may also be associated with a malignant solid tumor other than cancer as long as it has a similar characteristics, such as, for example, sarcomas including fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma and osteosarcoma, which are also within the scope of the present invention.

CAF may be present in various organs where aforementioned cancers are present, for example, in brain, head and neck, chest, limbs, lung, heart, thymus, esophagus, stomach, small intestine (duodenum, jejunum, ileum), large intestine (colon, cecum, appendix, rectum), liver, pancreas, gallbladder, anal, kidney, urinary duct, bladder, prostate, penis, testis, uterus, ovary, vulva, vagina, skin, striated muscle, smooth muscle, synovial membrane, cartilage, bone, thyroid, adrenal gland, peritoneum, mesenterium, etc.

A "tumor" herein includes a benign tumor and a malignant tumor (cancer). In the present invention, a "cancer" encompasses both epithelial and non-epithelial malignant tumors, and includes without being limited, for example, sarcomas such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma and osteosarcoma; carcinomas such as brain tumor, head and neck cancer, breast cancer, lung cancer, esophageal cancer, gastric cancer, duodenal cancer, appendiceal cancer, colorectal cancer, rectal cancer, hepatic cancer, pancreatic cancer, gallbladder cancer, bile duct cancer, anal cancer, renal cancer, ureteral cancer, bladder cancer, prostate cancer, penile cancer, testicular cancer, uterine cancer, ovarian cancer, vulvar cancer, vaginal cancer and skin cancer, and it further includes leukemia and malignant lymphoma, and the like.

A tumor cell in the present invention may be present in any site of the body including, for example, in brain, head and neck, chest, limbs, lung, heart, thymus, esophagus, stomach, small intestine (duodenum, jejunum, ileum), large intestine (colon, cecum, appendix, rectum), liver, pancreas, gallbladder, anal, kidney, urinary duct, bladder, prostate, penis, testis, uterus, ovary, vulva, vagina, skin, striated muscle, smooth muscle, synovial membrane, cartilage, bone, thyroid, adrenal gland, peritoneum, mesenterium, bone marrow, blood, vascular system, lymphatic system such as lymph nodes, and lymph fluid.

An "STRA6-expressing cell" herein means a cell expressing STRA6 on cell surface. STRA6 (stimulated by retinoic acid 6) is a high affinity receptor for RBP (retinol binding protein) present on cell surface. Therefore, the targeting molecule of the present invention which is based on a peptide comprising an amino acid sequence of the cell-binding region of RBP is considered to have a targetability to STRA6-expressing cells. STRA6 is considered to have a function of taking up retinol transported by RBP into a cell. It has been confirmed that STRA6 is expressed in cancer cells (e.g., colorectal cancer cells), retinal pigment epithelial (RPE) cells, Sertoli cells and astrocytes, etc. (Sun and Kawaguchi, Int Rev Cell Mol Biol. 2011; 288:1-41).

The nucleotide sequences of STRA6 have been known (e.g., GenBank Accession Nos. AY359089, AY358748 (human), NM_001029924 (rat), AF062476 (murine)), and antibodies have also been developed. Therefore, the expression of STRA6 can be detected by known techniques for detecting a nucleic acid or protein including, without being limited, for example, immunoprecipitation utilizing an anti-STRA6 antibody, EIA (enzyme immunoassay) (e.g., ELISA (enzyme-linked immunosorbent assay), etc.), RIA (radio immuno assay) (e.g., IRMA (immunoradiometric assay), RAST (radioallergosorbent test), RIST (radioimmunosorbent test), etc.), Western blotting, Immunohistochemistry, immunocytochemistry, flow cytometry, various hybridization method utilizing a nucleic acid coding for STRA6 or its unique fragment or a transcript (e.g., mRNA) or a nucleic acid which specifically hybridizes to a spliced product of said nucleic acid, Northern blotting, Southern blotting, and various PCR techniques. STRA6 expression is detected preferably at protein level, though it can alternatively be detected at genetic level. Therefore, the "STRA6-expressing cell" in the present invention includes not only the cells known to express STRA6 but also any cell in which STRA6 expression is confirmed by techniques as above.

In one embodiment, the target cell is selected from the group consisting of a stellate cell, a myofibroblast, a cancer-associated fibroblast and a tumor cell. In particular embodiment, the target cell is selected from the group consisting of a stellate cell, a myofibroblast and a cancer-associated fibroblast. In further particular embodiment, the target cell is selected from the group consisting of a stellate cell and a myofibroblast.

A "RBP" herein refers to serum RBP, an extracellular protein being present in blood. RBP is a known protein whose presence has been confirmed in various animal species, and its nucleic acid sequence is available from databases such as GenBank. For instance, the nucleic acid sequence of human RBP is registered under GenBank Accession No. NM_006744 (SEQ ID NO: 1), and the amino acid sequence under GenBank Accession No. NP_006735 (SEQ ID NO: 2), respectively. Nevertheless, since there could be possible mutations in the amino acid sequence or the nucleotide sequence occurring among individual organisms which does not interfere the physiological function of the protein, RBP or RBP gene in the present invention is not limited to the nucleic acid or protein having a sequence identical to the known sequence, but may include those having sequences different from said sequence in one or more bases or amino acids, typically one to several bases or amino acids, for example one, two, three, four, five, six, seven, eight, nine or ten bases or amino acids. RBP in the present invention may be of any animal species, preferably a vertebrate, more preferably a mammalian, particularly preferably human RBP.

The "cell-binding region of RBP" herein means a region of RBP which is involved in the binding to a target cell in the present invention In one embodiment, the cell-binding region of RBP is selected from the group consisting of Loops 1-3 and their functional fragments. Loops 1-3 are the loop-shaped structures protruding around the opening of RBP pocket which accommodates retinol. In human RBP, for instance, they are constituted by amino acid residues 46-59, 75-89, and 107-121, respectively, of the amino acid sequence of SEQ ID NO: 2. Functional fragments of Loops 1-3 are those among the fragments of Loops 1-3 which have the targetability to the target cell and which can be found, for example, by generating more than one different fragments of Loops 1-3 as described in Example 2 of the present specification and investigating whether they have the targetability to the target cell. For instance, a particular embodiment of the functional fragment of human RBP Loop 1 in the present invention is a fragment comprising an amino acid sequence of SEQ ID NO: 6, which is the minimum functional region.

In a preferred embodiment, the cell-binding region of RBP is selected from the group consisting of Loop 1, Loop 2, and their functional fragments. In more preferred embodiment, the cell-binding region of RBP is selected from the group consisting of Loop 1 and its functional fragment. In a particular embodiment, Loop 1 and Loop 2 are of human RBP and have amino acid sequences of SEQ ID NOS: 3 and 4, respectively. In a particular embodiment, the functional fragment of human RBP Loop 1 consists of an amino acid sequence selected from SEQ ID NOS: 6-13.

A "peptide comprising an amino acid sequence of the cell-binding region of RBP" herein (hereinbelow may be abbreviated as "cell binding region-containing peptide") includes the amino acid sequence of the cell-binding region of RBP as described above, and at the same time means any peptide that has a targetability to the target cell. Therefore, said peptide not only consists of the amino acid sequence of the cell-binding region of RBP but also includes those which contain additional amino acid sequences at N-terminal, C-terminal, or both N- and C-terminals of the amino acid sequence of the cell-binding region of RBP. The additional amino acid sequence includes any sequence which does not cause a loss of targetability of the peptide. Whether the additional amino acid sequence would cause a loss of targetability of the peptide or not can be assessed by, for example, an experimental comparison of targetability between a peptide comprising the additional amino acid sequence and the amino acid sequence of the cell-binding region of RBP, a peptide consisting solely of the amino acid sequence of the cell-binding region of RBP, and a peptide comprising no amino acid sequence of the cell-binding region of RBP, or by structural analysis or structure prediction of a peptide comprising the additional amino acid sequence. For instance, the additional amino acid sequence can be evaluated to cause a loss of the targetability of the peptide if the deliverability (i.e., an ability to deliver a substance bound to the peptide to a target cell) of the peptide comprising the additional amino acid sequence and the amino acid sequence of the cell-binding region of RBP is lower than the deliverability of the peptide consisting solely of the amino acid sequence of the cell-binding region of RBP and at the same time if it is equal to or less than the deliverability of the peptide comprising no amino acid sequence of the cell-binding region of RBP, or if it is obvious from the structural analysis or structure prediction that the additional amino acid sequence would mask cell-binding region of RBP.

The cell binding region-containing peptide is typically 10 amino acid long or more, preferably 10-50 amino acid long, more preferably 10-30 amino acid long, further preferably 10-20 amino acid long, in particular 10-14 amino acid long.

The cell binding region-containing peptide may be modified as long as the modification does not cause a loss of the targetability of the peptide. Whether the modification would cause a loss of the targetability of the peptide or not can be assessed, for example, by an experimental comparison of targetability between an unmodified cell binding region-containing peptide, a modified cell binding region-containing peptide, and an unmodified peptide comprising no cell-binding region. For instance, if the deliverability of the modified cell binding region-containing peptide is lower than the deliverability of the unmodified cell binding region-containing peptide and at the same time equal to or less than the targetability of the unmodified peptide comprising no cell-binding region, the modification can be evaluated to cause a loss of the targetability of the peptide. The modification may be carried out to all amino acids or to some amino acids of the peptide. When the modification is carried out to some amino acids, it may be carried out to amino acids of particular types or to amino acids at particular sites. Although it is not intended to limit the type or site of the amino acid to be modified, it is highly likely that a modification to an amino acid that is not within the minimum functional region of the cell binding region-containing peptide will not cause a loss of the targetability of the peptide. Non-limiting examples of modifications to the cell binding region-containing peptide include, for example, biotinylation, myristoylation, octanoylation, palmitoylation, acetylation, maleimidation, methylation, malonylation, amidation, esterification, farnesylation, geranylation, phosphorylation, sulfation, palmitoleoylation, PEGylation, and an addition of various labels (e.g., those described herein).

A "mutant peptide of the peptide having an equal targetability to a peptide comprising an amino acid sequence of the cell-binding region of RBP" herein (hereinbelow may be abbreviated as a "mutant peptide") encompasses any peptide having one or more (e.g., several) amino acid mutations in the cell binding region-containing peptide, in particular in its cell-binding region, and having a targetability equal to or greater than said peptide. Mutations include, for example, a deletion, substitution or addition of an amino acid or amino acids, and the number of amino acids to be mutated may be, for example, in the range from 1 to 10, from 1 to 9, from 1 to 8, from 1 to 7, from 1 to 6, from 1 to 5, from 1 to 4, from 1 to 3, from 1 to 2, when the mutation is carried out in the cell-binding region. More specifically, the number of amino acids to be mutated in the cell-binding region may be, for example, 1, 2, 3, 4, 5, 6, 7, 8, 9 or 10. When the mutation is carried out in a part which is not within the cell-binding region of the cell binding region-containing peptide, the number of amino acids to be mutated may be greater than the number mentioned above for the mutation in the cell-binding region, as long as the part will not cause a loss of the targetability of the peptide.

A substitution of an amino acid may be a conservative substitution. A conservative substitution is a well known concept in the field of the art, meaning a substitution of an original amino acid with another amino acid having a similar physicochemical properties such that the substitution would not substantially alter the function of the peptide. Since physicochemical properties of an amino acid is characterized by its side chains, an example of conservative substitution includes a substitution by an amino acid having a side chain that belongs to the same group with the original amino acid. An amino acid can be classified by the structure and characteristics of its side chain into either the group having a basic side chain (such as lysine, arginine and histidine), the group having an acidic side chain (such as aspartic acid and glutamate), the group having a non-charged polar side chain (such as asparagine, glutamine, serine, threonine, tyrosine), or the group having a non-polar side chain (such as glycine, alanine, valine, leucine, isoleucine, proline, phenylalanine, methionine, tryptophan and cysteine). Therefore, a conservative substitution includes a substitution between amino acids which belong to the same group described above. Non-limiting examples of the conservative substitution include, for example, a substitution between amino acids within each of the groups consisting of lysine and arginine; serine and threonine; glutamate and aspartic acid; glutamine and asparagine; or valine and leucine and isoleucine.

Whether or not a mutant peptide has a targetability equal to or greater than that of the cell binding region-containing peptide can readily be confirmed, without being limited, for example by following means: a mutant peptide or a cell binding region-containing peptide with a label or a drug added thereto, or a mutant peptide or a cell binding region-containing peptide bound to a composition comprising a label or a drug is added to a culture of a target cell, and the localization of the label or the effect of the drug is compared after predetermined time between the case in which the mutant peptide was added to the target cell and the case in which the cell binding region-containing peptide was added. If the level of the label or the action of the drug upon the addition of the mutant peptide is similar to or greater than that of the case where the cell binding region-containing peptide was added, the mutant peptide is considered to have a targetability equal to or greater than that of the cell binding region-containing peptide.

A "peptide mimetic" herein means a substance which has an equal characteristic or function to a given peptide (in particular, a naturally occurring α-peptide), especially a substance which can mimic a spatial arrangement of functional groups that is equal to the topology of the side chains of the given peptide. Peptide mimetics include, without being limited, such as, for example, a retro-inverso peptide. A retro-inverso peptide is a peptide in which amino acids having an opposite chirality to the amino acids of the reference peptide (e.g., D-amino acids when the amino acids in the reference peptide are L-amino acid) are bound in opposite order to the amino acid sequence of the reference peptide, and which has a similar side-chain topology as the reference peptide.

The targeting molecule of the present invention can be produced by any known method for producing a peptide or a peptide mimetic including, without being limited, for example, methods of chemical synthesis such as solid-phase synthesis and liquid-phase synthesis, and synthesis by genetic engineering (see, e.g., N. Leo Benoiton, Chemistry of Peptide Synthesis, CRC Press, 2005).

Another aspect of the present invention relates to a targeting agent (or a targeting composition) comprising a targeting molecule of the present invention for targeting a target cell selected from the group consisting of a stellate cell, a myofibroblast, a cancer-associated fibroblast, a tumor cell and an STRA6-expressing cell.

An "agent" and a "composition" are herein used interchangeably to mean a mixture of more than one ingredients (e.g., compounds). An "agent" and a "composition" may be directed to a particular application and, in that case, may appropriately comprise ingredients suitable for the application.

The targeting agent of the present invention has an ability to promote delivery of a substance bound thereto to a target cell (targetability). Here, the targetability means a similar ability as those mentioned for the targeting molecule of the present invention, namely an ability to deliver a substance quickly and/or in a large amount and/or to allow it being take up, as compared to the case without the targeting agent.

The targeting agent of the present invention may comprise, adding to the targeting molecule of the present invention, an ingredient useful for the interaction with the substance to be delivered to the target cell (e.g., a drug, carrier or label) such as, without being limited, for example, a linker. The linker is not particularly limited as long as it can bind the targeting molecule with the substance to be delivered, and any known linkers may be used. Examples of the linker that could be contained in the targeting agent of the present invention include, for example, peptide linkers such as Glycine-Glycine-Glycine (triglycine), non-peptide linkers such as glycerol, polyethylene glycol, polypropylene glycol ethylene glycol-propylene glycol copolymer, polyvinyl alcohol, monosaccharides, polysaccharides, polyester, polyether and biodegradable polymers such as polylactic acid.

Another aspect of the present invention relates to a carrier which delivers a substance to a target cell selected from the group consisting of a stellate cell, a myofibroblast, a cancer-associated fibroblast, a tumor cell and an STRA6-expressing cell, wherein the carrier has been targeted with the targeting molecule of the present invention. Hereinbelow, a carrier which has been targeted with the targeting molecule of the present invention may be referred to as a "targeting carrier" whereas a carrier which has not been targeted with the targeting molecule of the present invention may simply be referred to as a "carrier" for distinction.

A "carrier" herein means a substance which facilitates the transport of one or more substance (e.g., a drug or label) carried by it from one part of the body to a target cell or tissue and/or within the target cell or tissue. The carrier may be constituted by a single compound or may be constituted by more than one homologous or heterologous compounds. In preferred embodiment, the carrier may include any known carriers which can be targeted using the targeting molecule of the present invention. The carrier that is capable of such targeting (i.e., active targeting) includes such as, without being limited, for example, carriers having a straight chain or branched linear structure such as polymeric carriers, and carriers having a particle structure such as liposomes, dendrimers, nanoparticles and macromolecular micelles (particle carriers) (e.g., Marcucci and Lefoulon, Drug Discov Today. 2004 Mar. 1; 9(5):219-28, Torchilin, Eur J Pharm Sci. 2000 October; 11 Suppl 2:S81-91). The carrier may be cationic or non-cationic (e.g., anionic or neutral). In one embodiment, the carrier is cationic. Moreover, the carrier may be capable of forming a lipoplex or polyplex with the substance being carried by it. A lipoplex can be formed, for example, between a cationic lipid and a substance having a negative charge (e.g., a nucleic acid such as a DNA), and a polyplex can be formed, for example, between a polycation and a substance having a negative charge, respectively.

The carrier of the invention may comprise as components, for example, without being limited, a lipid or polymer.

Non-limiting examples of the lipid include phospholipids such as glycerophospholipid, sphingolipids such as sphingomyelin, sterols such as cholesterol, plant oils such as soy bean oil and poppy oil, mineral oils and lecithin such as egg yolk lecithin. More specific examples of the lipid include such as dimyristoylphosphatidylcholine (DMPC), dipalmitoylphosphatidylcholine (DPPC), distearoylphosphatidylcholine (DSPC), dioleylphosphatidylethanolamine (DOPE), dilauroylphosphatidylcholine (DLPC), sterols such as cholesterol, N-(α-trimethylammonioacetyl)-didodecyl-D-glutamate chloride (TMAG), N,N',N'',N''-tetramethyl-N,N',N'',N''-tetrapalmitylspermine (TMTPS), 2,3-dioleyloxy-N-[2(spermine carboxamide)ethyl]-N,N-dimethyl-1-propaneaminiumtrifluoroacetate (DOSPA), N-[1-(2,3-dioleyloxy)propyl]-N,N,N-trimethylammonium chloride (DOTMA), dioctadecyldimethylammonium chloride (DODAC), didodecylammonium bromide (DDAB), 1,2-dioleyloxy-3-trimethylammoniopropane (DOTAP), 3β-[N—(N',N'-dimethylaminoethane) carbamoyl]cholesterol (DC-Chol), 1,2-dimyristoyloxypropyl-3-dimethylhydroxyethylammonium bromide (DMRIE), O,O'-ditetradecanoyl-N-(α-trimethylammonioacetyl)diethanolamine chloride (DC-6-14). The lipid may be a cationic lipid or non-cationic lipid, e.g., an anionic lipid or neutral lipid. In one embodiment, the carrier of the present invention comprises a cationic lipid. The cationic lipid is particularly useful for introducing a negatively charged nucleic acid and the like into a cell.

Other non-limiting examples of the lipid include such as the cationic lipid and PEG-bound lipid (PEG-lipid) described in WO 2012/170952, and the ionizable lipid described in WO 2013/185116. Said cationic lipid is a compound represented by formula I:

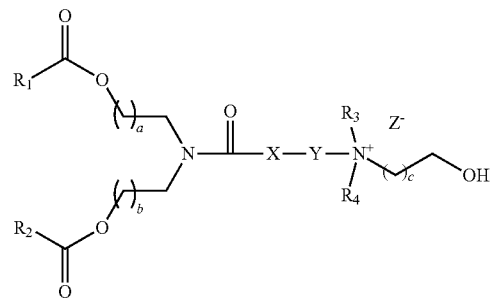

wherein, $R_1$ and $R_2$ are independently selected from the group consisting of $C_{10}$-$C_{18}$ alkyl, $C_{12}$-$C_{18}$ alkenyl and oleyl groups, $R_3$ and $R_4$ are independently selected from the group consisting of $C_1$-$C_6$ alkyl and $C_2$-$C_6$ alkanol, X is either selected from the group consisting of —$CH_2$—, —S— and —O—, or absent, Y is selected from the group consisting of —$(CH_2)_n$—, —$S(CH_2)_n$—, —$O(CH_2)_n$—, thiophene, —$SO_2(CH_2)_n$— and an ester, n=1 to 4, a=1 to 4, b=1 to 4, c=1 to 4, and Z is a counter ion.

Non-limiting examples of said cationic lipid include, for example, followings:

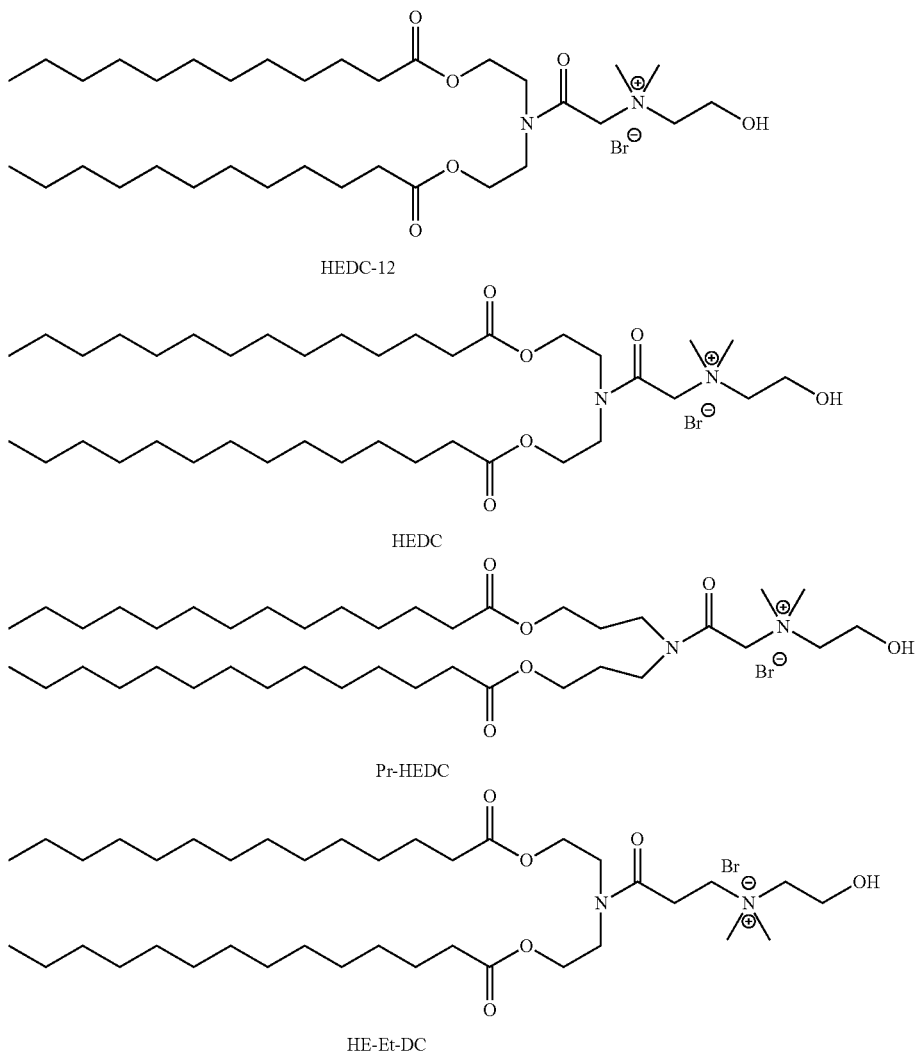

-continued
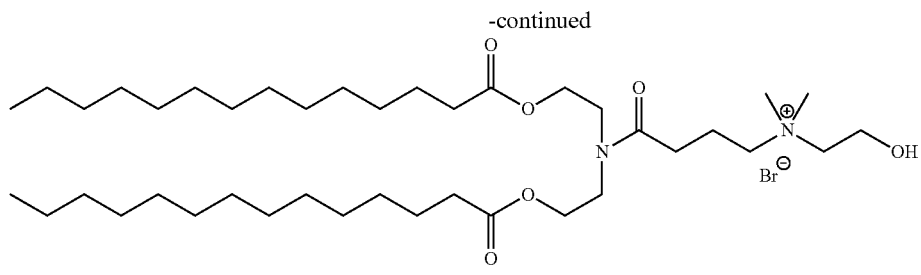
HE-Pr-DC
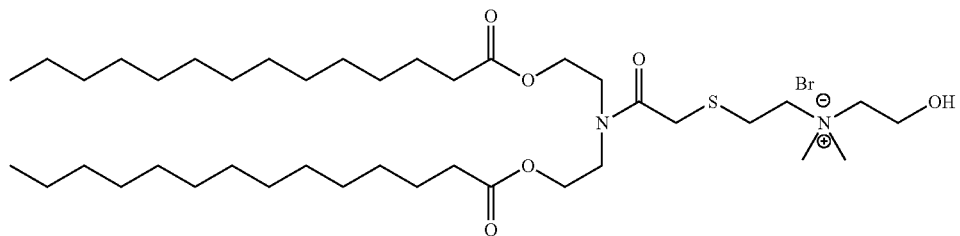
HES104
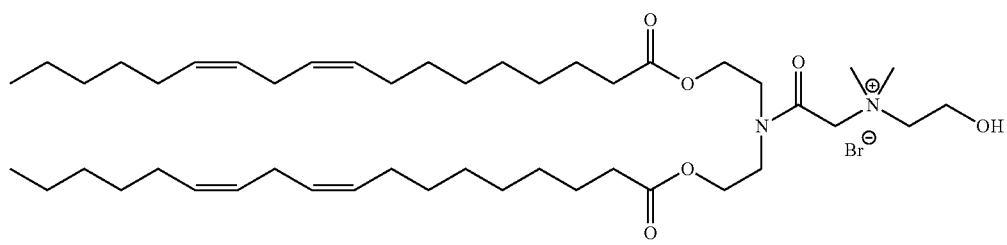
HE-DODC-DLin
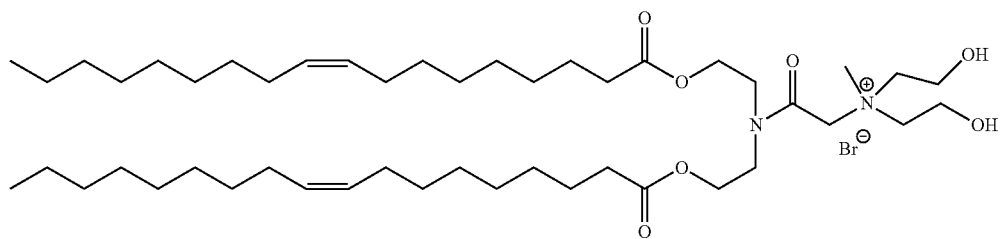
HE2-DODC
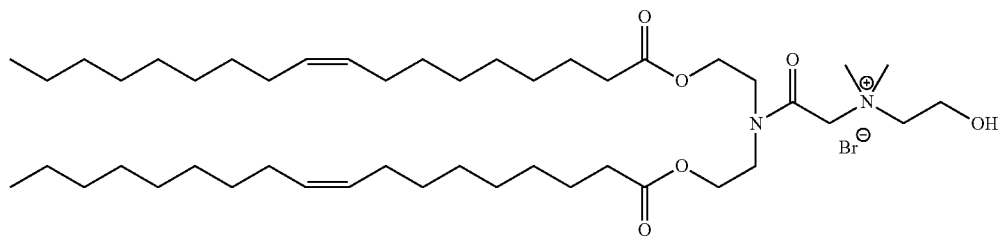
HE-DODC
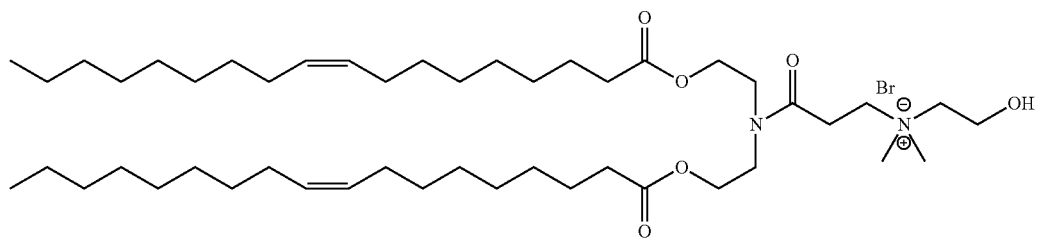
HE-Et-DODC

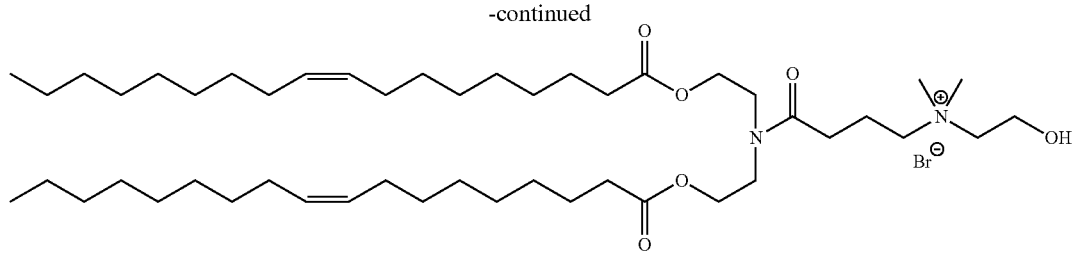
HE-Pr-DODC
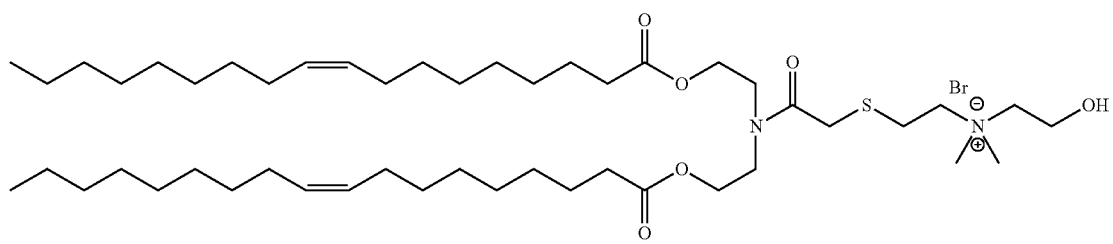
HES104DO
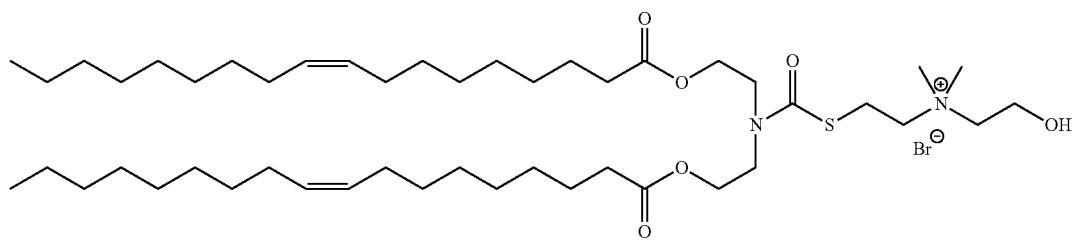
HETU104DO

Non-limiting examples of said PEG-lipid include such as, for example, 1,2-dimyristoyl-sn-glycero-3-phosphoethanolamine-N-PEG (PEG-DMPE), 1,2-dipalmitoyl-sn-glycero-3-phosphoethanolamine-N-PEG (PEG-DPPE), 1,2-distearoyl-sn-glycero-3-phosphoethanolamine-N-PEG (PEG-DSPE), 1,2-dioleoyl-sn-glycero-3-phosphoethanolamine-N-PEG (PEG-DOPE) and PEG ceramide. The molecular weight of PEG is not particularly limited and may be, for example, from about 550 to about 2000, more specifically about 550, about 750, about 1000, about 1250, about 2000. The non-limiting examples of PEG include such as, for example, PEG 550, PEG 750, PEG 1000, PEG 1250 and PEG 2000.

Said ionizable lipid is a compound represented by formula II:

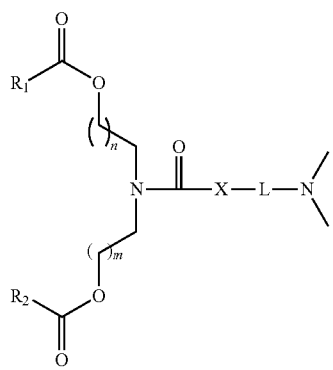

II wherein, n and m is independently 1, 2, 3 or 4, $R_1$ and $R_2$ is independently $C_{10}$-$C_{18}$ alkyl or $C_{12}$-$C_{18}$ alkenyl, X is —$CH_2$—, S, O, N or absent, L is $C_{1-4}$ alkylene, —S—$C_{1-4}$ alkylene, alkylene, —O—O(O)—$C_{1-4}$ alkylene, —S(O)$_2$—$C_{1-4}$ alkylene,

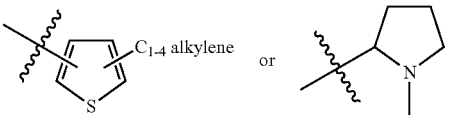

or a pharmaceutically acceptable salt thereof.

Non-limiting examples of said ionizable lipid include, for example, followings:

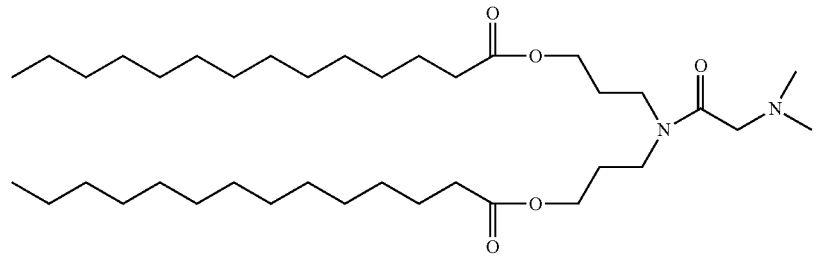

i-Pr-DC

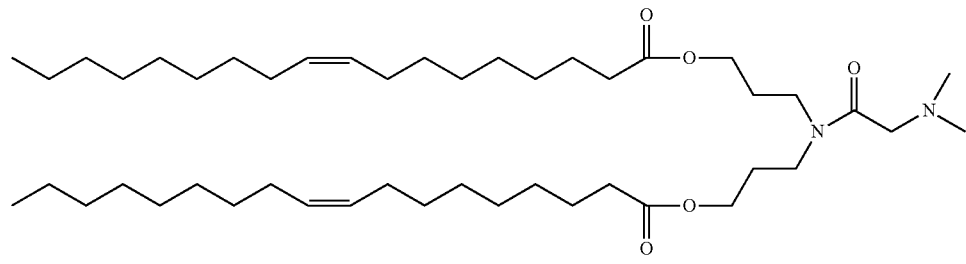

i-Pr-DODC

-continued
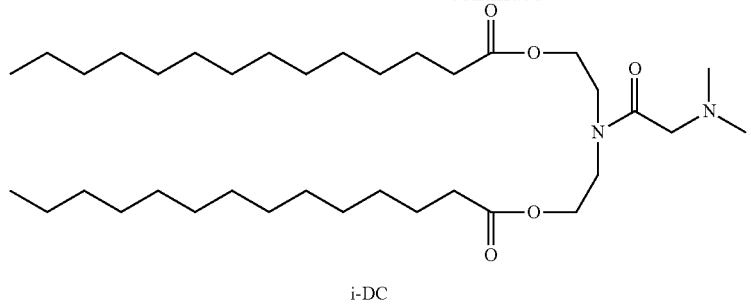
i-DC
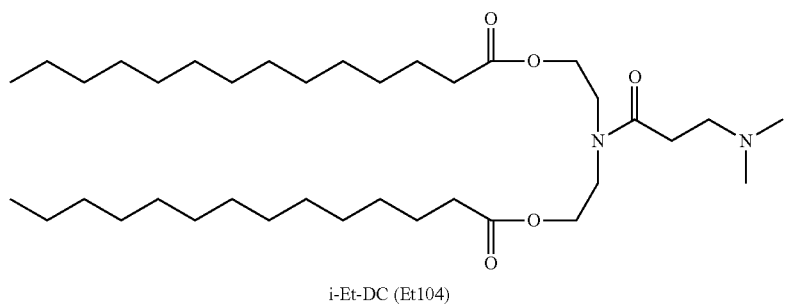
i-Et-DC (Et104)
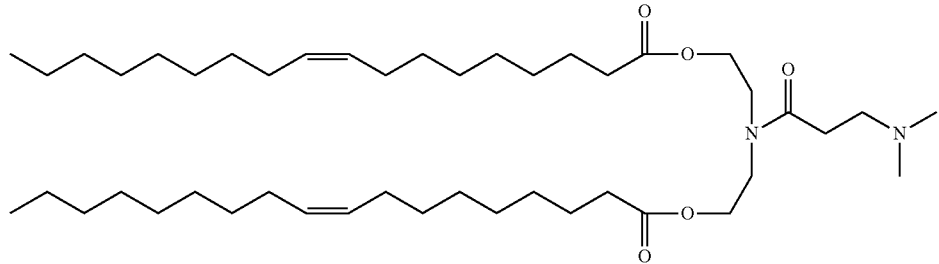
i-Et-DODC
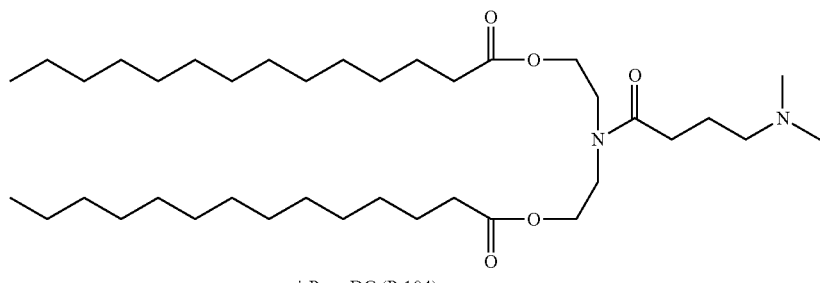
i-Prop-DC (Pr104)
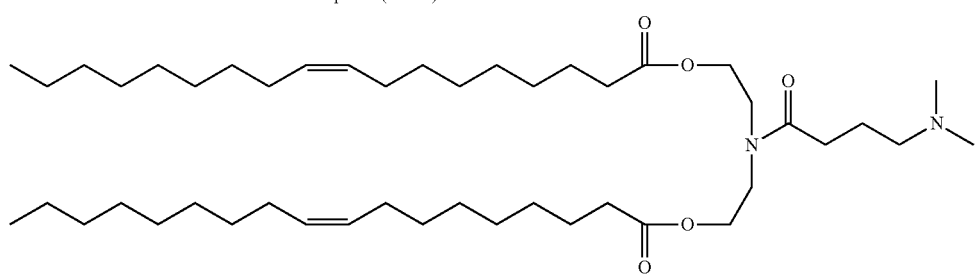
i-Prop-DODC (Pr104-DO)

-continued
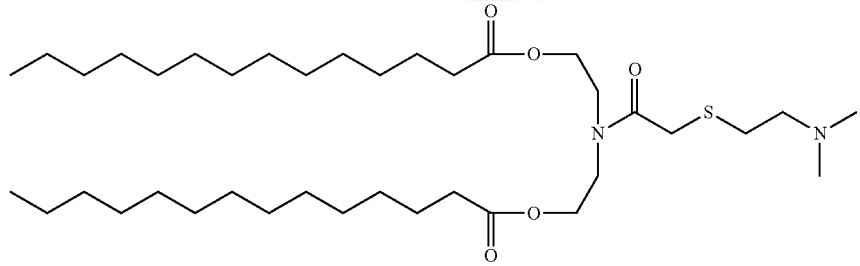
S104
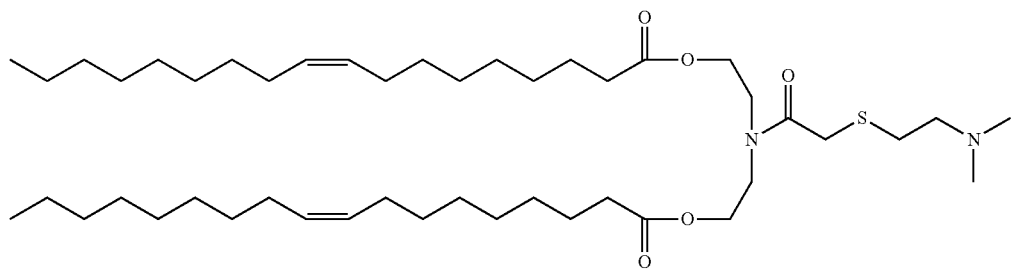
S104-DO
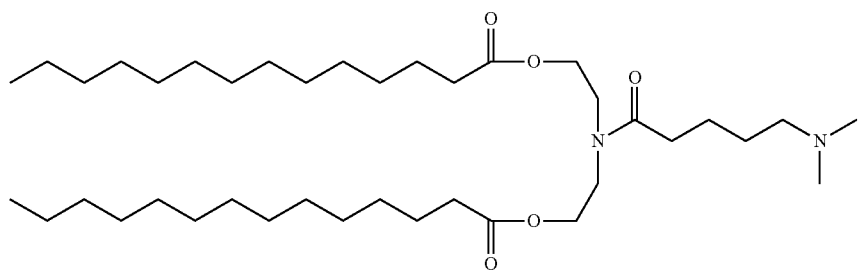
C104
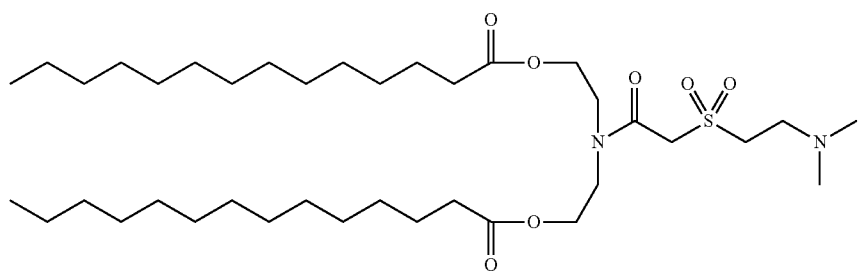
SO2-S104
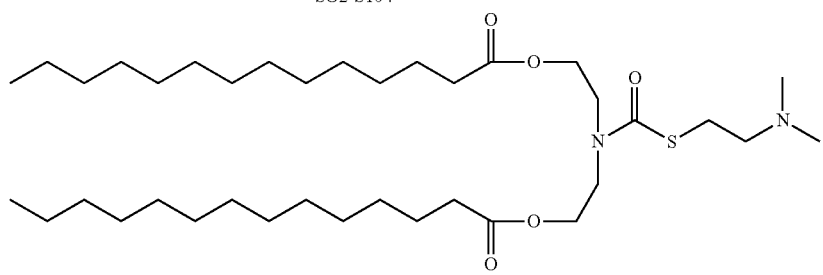
TU104

-continued
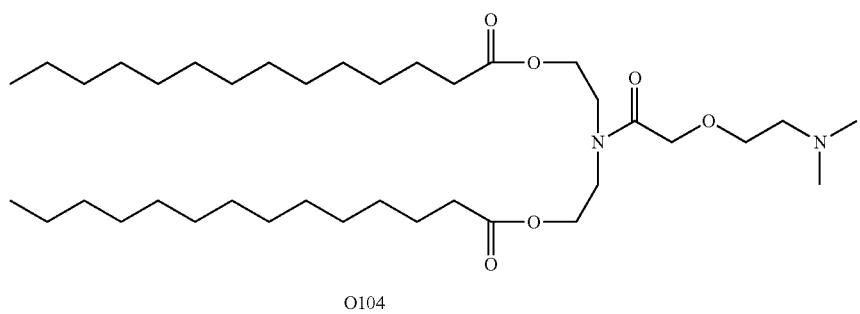
O104
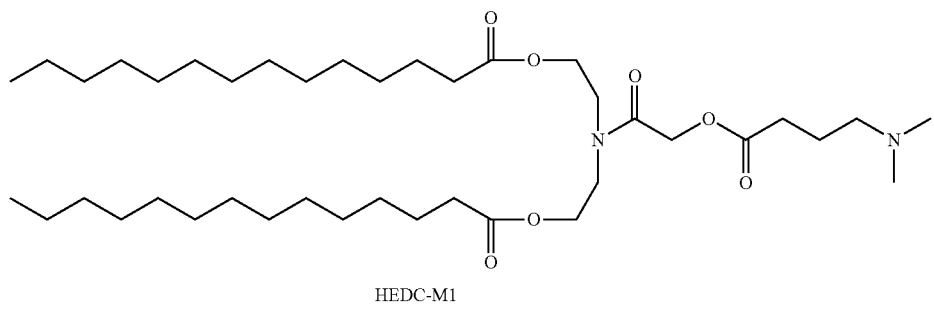
HEDC-M1
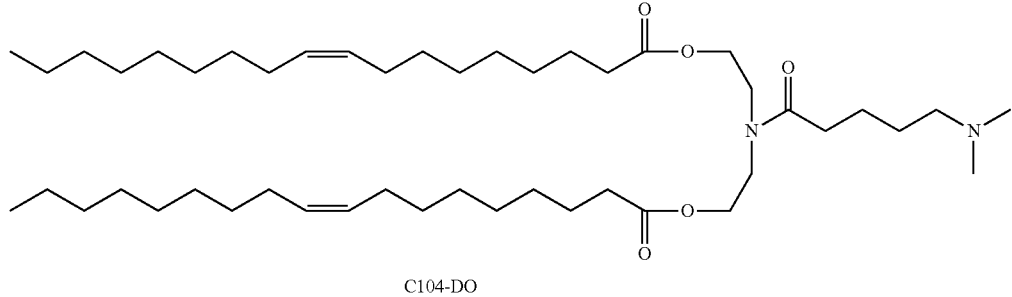
C104-DO
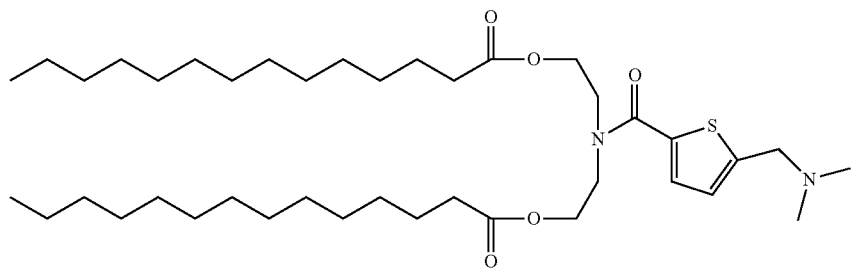
T104
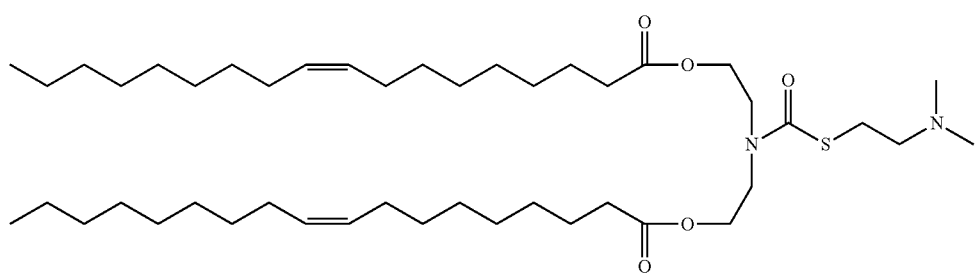
TU104-DO -continued
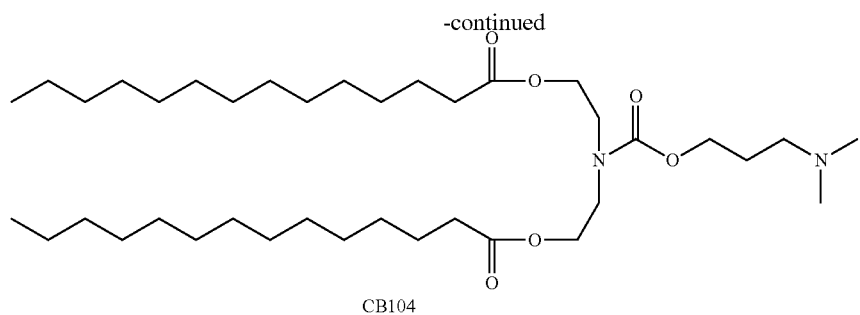
CB104
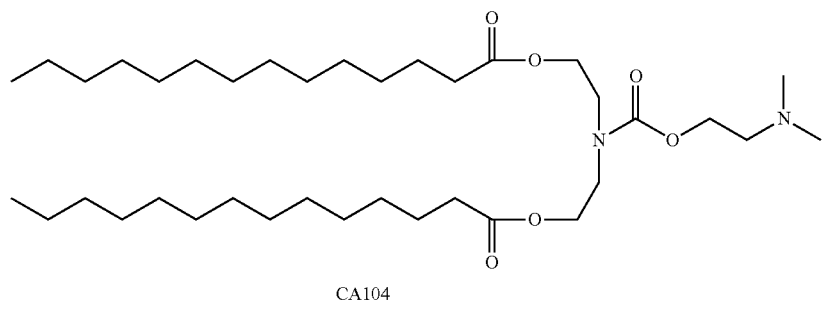
CA104
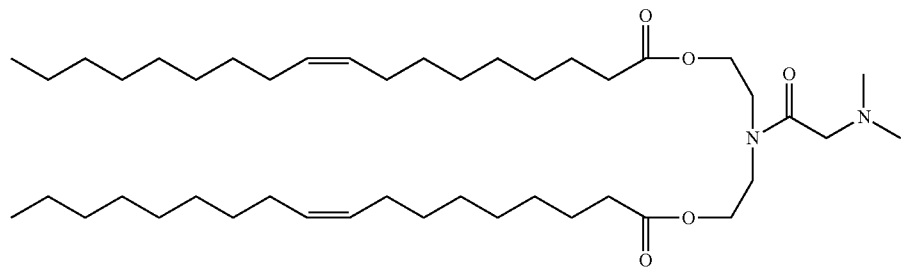
INT-4
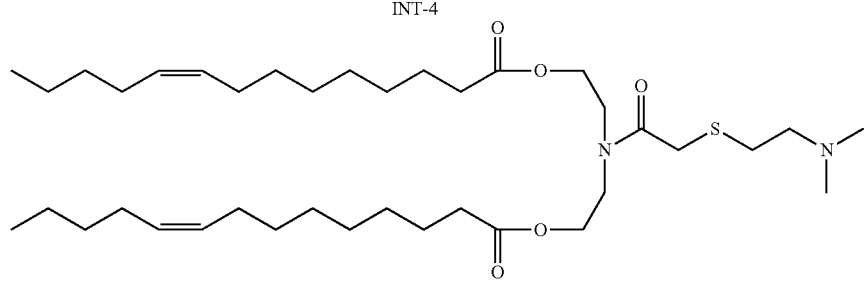
S104-DMO
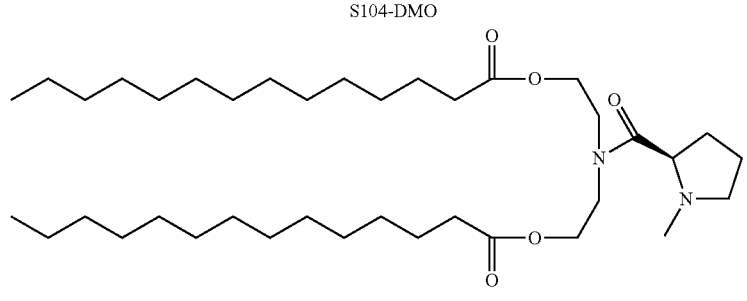
Pro-DC

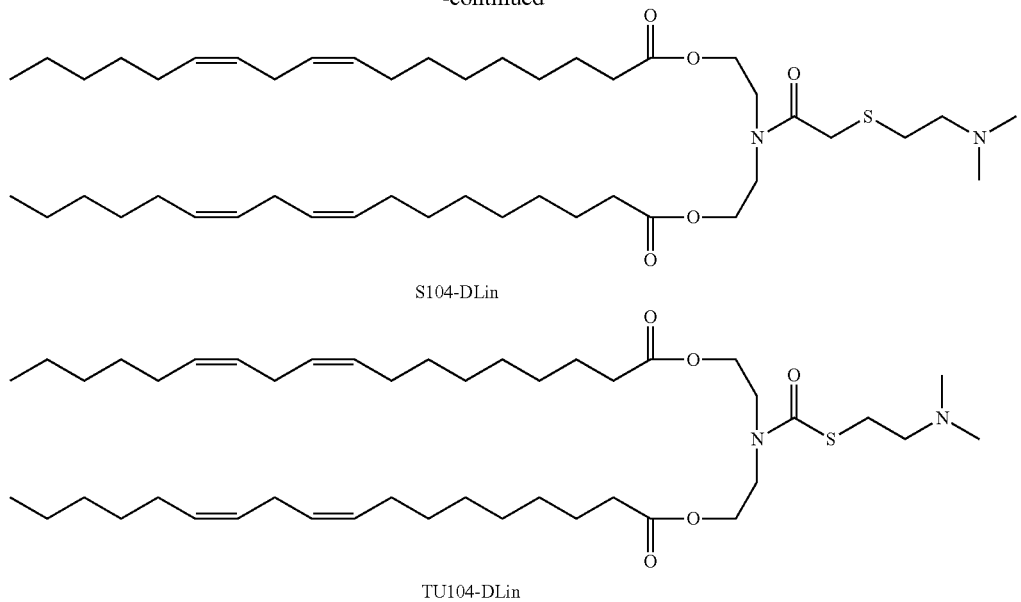

S104-DLin

TU104-DLin

The carrier of the present invention may comprise one or more lipids. In one embodiment, the carrier of the present invention comprises a cationic lipid and an ionizable lipid. In particular embodiment, the carrier of the present invention comprises a cationic lipid, an ionizable lipid and a PEG-lipid. Non-limiting examples of the combination of lipids contained in the carrier of the present invention include such as, for example, a combination of HEDC and S104, a combination of HEDC, S104, DOPE, cholesterol and PEG-DMPE, a combination of DODC, DOPE, cholesterol and PEG-lipid, the combination of HEDODC, DOPE, cholesterol and PEG-lipid, and a combination of DC-6-14, DOPE and cholesterol. Specific non-limiting examples of the combination of lipids contained in the carrier of the present invention include such as, for example, HEDC:S104 (1:1 molar ratio), HEDC:S104:DOPE:cholesterol:PEG-DMPE (4:4:6:5:1 molar ratio), DODC:DOPE:cholesterol:PEG-lipid (25:5:19:1 molar ratio), HEDODC:DOPE:cholesterol:PEG-lipid (25:5:19:1 molar ratio), and DC-6-14:DOPE:cholesterol (4:3:3 molar ratio).

Non-limiting examples of the polymer include cationic polymers (polycation) such as polyethylene glycol (PEG), polyethylene imine (PEI) and polylysine (e.g., poly-L-lysine (PLL)), non-cationic polymers such as polylactic acid (PLA), polyglycolic acid (PGA), lactic acid-glycolic acid copolymer (PLGA), and/or those based on derivatives thereof.

In the present invention, "being targeted with the targeting molecule" means that the targeting molecule is in an interaction (e.g., binding) with a substance to be guided to the target cell (e.g., a substance to be delivered such as a carrier, a drug or a label) in a manner such that the targeting molecule can exert its targetability. Non-limiting examples of the interaction between the targeting molecule and the substance to be guided to the target cell include, for example, any known chemical bonds such as a covalent bond, an ionic bond, an electrostatic bond, a hydrophobic bond, van der Waals force and an avidin-biotin bond. The targeting molecule may be present in a manner that at least its part involved in the interaction with the target cell (e.g., functional moieties of RPB Loops 1-3, in particular, the functional moiety of Loop 2 comprising the amino acid sequence of SEQ ID NO: 6) is exposed outside the substance to be guided to the target cell such that the interaction with the target cell can occur, for example. Means for exposing at least the part of the targeting molecule involved in the interaction with the target cell outside of the carrier include such as, for example, mixing the targeting molecule with the substance to be guided to the target, or binding the targeting molecule to the substance to be guided to the target.

The targeting carrier of the present invention may be targeted with one or more targeting molecules. In one embodiment, the targeting carrier of the present invention is targeted with the targeting molecule in an amount effective for targeting to the target cell. Specific amount of the targeting molecule effective for the targeting of the targeting carrier of the present invention (e.g., the molar ratio relative to the carrier component) can be determined, for example, by investigating the targetability of the carrier targeted by different amounts of the targeting molecule using procedures described in Example 2. The amount of the targeting molecule effective for the targeting of the targeting carrier of the present invention may be, without being limited, for example, a molar ratio of 1000:1 to 1:1000, 100:1 to 1:100, 50:1 to 1:50, 40:1 to 1:40, 30:1 to 1:30, 25:1 to 1:25, 20:1 to 1:20, 10:1 to 1:10, 8:1 to 1:8, 6:1 to 1:6, 5:1 to 1:5, 4:1 to 1:4, 3:1 to 1:3 or 2:1 to 1:2 relative to the component of the carrier (if the carrier comprises more than one components, the main component).

The substance carried by the targeting carrier of the present invention is not particularly limited, but preferably in a size such that it can physically be transported in the body of the organism from site of administration to the site where the target cell is present. Therefore, the targeting carrier of the present invention can transport not only an atom, a compound, a protein or a nucleic acid, but also an object such as a vector, virus particles, a cell, a drug delivery system composed of one or more element, or a micromachine. Said substance to be delivered preferably has a characteristic that has some influences on the target cell and includes, for example, a substance which labels the target cell (e.g., a label) or a substance which controls (e.g., enhances or suppresses) the activity or proliferation of the target cell (e.g., a drug).

The targeting by the targeting molecule in the targeting carrier of the present invention can be achieved, for example, by mixing the carrier with the targeting molecule in a predetermined ratio or by binding the targeting molecule to the component of the carrier. Various methods are known for binding the targeting molecule to the carrier (e.g., Torchilin, Nat Rev Drug Discov. 2005 February; 4(2):145-60, Nobs et al., J Pharm Sci. 2004 August; 93(8):1980-92, Marcucci and Lefoulon, 2004, supra). The binding of the targeting molecule to the component of the carrier may be carried out after the preparation of the carrier, or may be carried out to predetermined component before the preparation of the carrier, or may be carried out during the preparation of the carrier. Moreover, the targeting molecule may be bound to the carrier component directly or via a linker.

Another aspect of the present invention relates to a complex represented by a formula:

X—Y—Z    (1)

wherein,

X is a targeting moiety comprising the targeting molecule of the present invention, Y is a binding moiety, and Z is a functional moiety comprising a substance selected from the group consisting of a drug, a label and a carrier.

The targeting moiety in the complex of the present invention may consist of the targeting molecule of the present invention or may be composed of the targeting molecule of the present invention and a connecting group, etc. attached thereto which is suitable for binding to the binding moiety. The targeting molecule of the present invention contained in the targeting moiety may be modified to be suitable for binding to the binding moiety to an extent at which its targetability is not lost. Connecting groups and modifications compatible with the chemical binding to a given substance are well known in the art (e.g., Torchilin, 2005, supla, Nobs et al., 2004, supla, Marcucci and Lefoulon, 2004, supla). Moreover, the targeting moiety may comprise a single targeting molecule or may comprise more than one targeting molecules. When the targeting moiety comprises more than one targeting molecules, the targeting molecules may be the same or different. Furthermore, the targeting moiety may be bound to a single functional moiety via a single binding moiety or may be bound to more than one functional moieties via more than one binding moieties. When the targeting moiety is bound to more than one binding moieties and/or functional moieties, the binding moieties and/or functional moieties may be the same or different.

The binding moiety in the complex of the present invention may be a chemical bond or a linker. The chemical bond includes any known chemical bonds such as a covalent bond, an ionic bond, an electrostatic bond, a hydrophobic bond, van der Waals force and an avidin-biotin bond. The linker is a chemical moiety which can bind the targeting moiety to the functional moiety by a chemical bond via itself. Linkers compatible with the chemical binding of predetermined two different substances are well known in the art. Non-limiting examples of the linker include such as, for example, peptide linkers such as Glycine-Glycine-Glycine (triglycine), non-peptide linkers such as glycerol, polyethylene glycol, polypropylene glycol ethylene glycol-propylene glycol copolymer, polyvinyl alcohol, monosaccharides, polysaccharides, polyester, polyether, and biodegradable polymers such as polylactic acid.

The binding moiety may be bound to a single targeting moiety or may be bound to more than one targeting moieties. Moreover, the binding moiety may be bound to a single functional moiety or may be bound to more than one functional moieties. When the binding moiety is bound to more than one targeting moieties and/or functional moieties, the targeting moieties or the functional moieties may be the same or different.

The drug contained in the functional moiety in the complex of the present invention is not particularly limited and includes any drugs associated with the target cell. Such drugs may interact with the target cell itself or may interact with the environment that surrounds the target cell, for example, non-target cells present around the target cell or intercellular substances (e.g., extracellular matrix). In one embodiment, the drug controls (e.g., suppresses, maintains or promotes) the activity or proliferation of the target cell. In particular embodiment, the drug suppresses the activity or proliferation of the target cell. Certain specific examples of such drugs include, without being limited, a TGFβ (Transforming growth factor-beta) inhibitor, HGF (Hepatocyte growth factor) or a substance promoting its production, a PPARγ (Peroxisome proliferator-activated receptor gamma) ligand, an angiotensin inhibitor, a PDGF (Platelet-derived growth factor) inhibitor, relaxin or a substance promoting its production, an inhibitor of the production and/or secretion of an extracellular matrix component, a cellular activity suppressing substance, a cell proliferation-suppressing substance, an apoptosis-inducing substance, a collagen degradation-promoting substance, an inhibitor of the collagen degradation-promoting substance, PAI-1 (Plasminogen activator inhibitor-1) inhibitor, an α1 antitrypsin inhibitor, an angiotensinogen inhibitor, and the like.

A TGFβ inhibitor includes, without limitation, such as, for example, inhibitors of TGFβ activity such as a truncated TGFβ type II receptor (Qi et al., Proc Natl Acad Sci USA. 1999; 96(5):2345-9), a soluble TGFβ type II receptor (George et al., Proc Natl Acad Sci USA. 1999; 96(22): 12719-24), anti-TGFβ antibodies, and TGFβ production inhibitors such as RNAi (RNA interference) molecules, ribozymes and antisense nucleic acids against TGFβ, and vectors expressing these. In one embodiment, a TGFβ inhibitor inhibits the activity and/or production of TGFβ1.

A promoter of HGF and relaxin production includes, without limitation, for example, nucleic acids encoding HGF and relaxin, expression constructs comprising the same, and expression vectors comprising these.

A PPARγ ligand includes, without limitation, such as, for example, endogenous ligands such as 15-deoxy-Δ12,14-prostaglandin J2, a nitrolinoleic acid, an oxidized LDL (Low density lipoprotein), a long-chain fatty acid and eicosanoid, and exogenous ligands such as thiazolidinedione drugs such as troglitazone, pioglitazone, rosiglitazone, balaglitazone and rivoglitazone, and nonsteroidal antiinflammatory drugs.

An angiotensin inhibitor includes, without limitation, such as, for example, angiotensin receptor antagonists such as telmisartan, losartan, valsartan, candesartan cilexetil, olmesartan medoxomil andirbesartan. Angiotensin includes angiotensin I, II, III and IV. Moreover, an angiotensin receptor includes, without limitation, such as, for example, angiotensin type 1 receptor (AT1).

A PDGF inhibitor includes, without limitation, such as, for example, inhibitors of PDGF activity such as an anti-PDGF antibody and inhibitors of PDGF production such as RNAi molecules, ribozymes and antisense nucleic acids against PDGF, and vectors expressing these.

A substance inhibiting the production and/or secretion of an extracellular matrix component includes, without limitation, for example, substances such as RNAi molecules, ribozymes and antisense nucleic acids that suppress the expression of extracellular matrix components such as collagen, proteoglycan, tenascin, fibronectin, thrombospondin, osteopontin, osteonectin and elastin, or substances having a dominant negative effect such as dominant negative mutant, and vectors expressing these. Drugs which inhibit collagen production/secretion include, without being limited, for example, inhibitors of HSP (Heat shock protein) 47, which is a collagen-specific molecular chaperone essential for the common processes during synthetic processes of various types of collagen, i.e., the intracellular transport and the maturation of the molecules, for example, inhibitors of HSP47 expression such as RNAi molecule (e.g., siRNA molecules described in WO 2011/072082), ribozymes, antisense nucleic acids against HSP47, or substances having a dominant negative effect such as a dominant negative mutant of HSP47, and vectors expressing these.

A cell proliferation-suppressing substance includes, without limitation, for example, alkylating agent (e.g., ifosfamide, nimustine, cyclophosphamide, dacarbazine, melphalan, ranimustine), antitumor antibiotics (e.g., idarubicin, epirubicin, daunorubicin, doxorubicin, pirarubicin, bleomycin, peplomycin, mitoxantrone, mitomycin C), antimetabolites (e.g., gemcitabine, enocitabine, cytarabine, tegafur-uracil, tegafur-gimeracil-oteracil potassium formulation, doxifluridine, hydroxycarbamide, fluorouracil, methotrexate, mercaptopurine), alkaloids such as etoposide, irinotecan, vinorelbine, docetaxel, paclitaxel, vincristine, vindesine and vinblastine, platinum complexes such as carboplatin, cisplatin and nedaplatin, and statins such as lovastatin, simvastatin.

A cellular activity suppressing substance includes, without limitation, for example, a sodium channel inhibitor such as amiloride.

An apoptosis-inducing agent includes, without limitation, such as, for example, Compound 861, gliotoxin and atorvastatin.

A collagen degradation-promoting substance includes, without limitation, such as, for example, various collagenase or promoters of their production. Examples of collagenase include, without being limited, such as, for example, those of MMP family such as MMP (Matrix metalloproteinase) 1, 2, 3, 9, 13 and 14. A promoter of collagenase production includes, without limitation, such as, for example, a nucleic acid encoding collagenase, expression constructs comprising these, and expression vectors comprising these.

An inhibitor of a collagen degradation-promoting substance includes, without limitation, such as, for example, TIMP (tissue inhibitor of metalloproteinase, e.g., TIMP1 and TIMP2). Therefore, a substance inhibiting said substance includes, without limitation, for example, inhibitors of TIMP activity such as an antibody against TIMP, inhibitors of TIMP production such as RNAi molecules (e.g., siRNA molecules described in WO 2012/044620), ribozymes and antisense nucleic acids against TIMP, and vectors expressing these.

A PAI-1 inhibitor includes, without limitation, for example, inhibitors of PAI-1 activity such as an antibody against PAI-1, inhibitors of PAI-1 production such as RNAi molecules, ribozymes and antisense nucleic acids against PAI-1, and vectors expressing these.

An α1-antitrypsin inhibitor includes, without limitation, for example, inhibitors of PAI-1 activity such as an antibody against α1-antitrypsin, inhibitors of al-antitrypsin production such as RNAi molecules, ribozymes and antisense nucleic acids against α1-antitrypsin, and vectors expressing these.

An angiotensinogen inhibitor includes, without limitation, for example, inhibitors of angiotensinogen activity such as an antibody against angiotensinogen, inhibitors of angiotensinogen production such as RNAi molecules, ribozymes and antisense nucleic acids against angiotensinogen, and vectors expressing these.

An RNAi molecule herein means any molecule having an RNAi activity and encompasses, without being limited, for example, RNAs such as an siRNA (small interfering RNA), miRNA (micro RNA), shRNA (short hairpin RNA), ddRNA (DNA-directed RNA), piRNA (Piwi-interacting RNA), rasiRNA (repeat associated siRNA) and variations thereof. Moreover, the nucleic acid herein includes an RNA, DNA, PNA, or a complex thereof.

The label herein refers to any substance that directly or indirectly allows itself or an object to which it attaches being detected. The label can be selected from any of those known to a person skilled in the art, for example, a gas or a substance which generate a gas under physiological condition, any radioisotopes, magnetic bodies, an element which develops nuclear magnetic resonance (e.g., hydrogen, phosphorus, sodium or fluorine), a substance which influences on the relaxation time of the element which develops nuclear magnetic resonance (e.g., a metal atom or a compound comprising it), a substance which binds to a labeling substance (e.g., antibody), fluorescent substances, fluorophores, chemiluminescent substances, enzymes, biotin or a derivative thereof, and avidin or a derivative thereof.

The label herein may be detectable, including any labels that can be detected by any existing means for detection. Detecting techniques include, without being limited, for example, a technique using a macroscopic, optical examination device (e.g., an optical microscope, fluorescent microscope, phase-contrast microscope, and in vivo imaging device), an X-ray device (e.g., a plain X-ray device, CT (computed tomography) device), an MRI (magnetic resonance imaging) device, a radioisotope examination device (scintigraphic device, a PET (positron emission tomography) device, a SPECT (single photon emission computed tomography) device), an ultrasonic examination device and a thermography device. The label suitable for each detecting technique is known to person skilled in the art and described in such as, for example, Lecchi et al., Q J Nucl Med Mol Imaging. 2007; 51 (2): 111-26.

The label suitable for the detection by a macroscopic and optical examination device includes, for example, various fluorescent and luminescent labels.

As specific fluorescent labels, without being limited, for example, Cy™ series (e.g., Cy™2, 3, 5, 5.5, and 7), DyLight™ series (e.g., DyLight™ 405, 488, 549, 594, 633, 649, 680, 750, and 800), Alexa Fluor® series (e.g., Alexa Fluor® 405, 405, 488, 549, 594, 633, 647, 680, and 750), HiLyte Fluor™ series (e.g., HiLyte Fluor™ 488, 555, 647, 680, and 750), ATTO series (e.g., ATTO488, 550, 633, 647N, 655, and 740), FAM, FITC, Texas Red, GFP, RFP, and Qdot may be used. Fluorescent labels suitable for in vivo imaging include, for example, those which have a high bio-permeability and which generate fluorescence at a wavelength that is not susceptive to autofluorescence, for example, near infrared wavelength, or those which have a strong fluorescence intensity. Such fluorescent labels include, without limitation, such as, for example, Cy™ series, DyLight™ series, Alexa Fluor® series, HiLyte Fluor™ series, ATTO series, Texas Red, GFP, RFP, Qdot and derivatives thereof.

As specific luminescent labels, without being limited, for example, luminol, luciferin, lucigenin and aequorin and the like may be used.

Labels suitable for the detection with an X-ray device include, for example, various contrast agents. As specific contrast agents, without being limited, for example, an iodine atom, an iodine ion, an iodine containing compound and the like may be used.

Labels suitable for the detection with an MRI device include, for example, an element which develops nuclear magnetic resonance, and a substance which influences on the relaxation time of the element which develops nuclear magnetic resonance. Elements which develop nuclear magnetic resonance include such as, for example, hydrogen, phosphorus, sodium and fluorine. Substances which influence on the relaxation time of the element which develops nuclear magnetic resonance include such as, without being limited, various metal atoms, and a compound comprising one or more of said metal atoms, for example, a complex of one or more of said metal atoms. Specifically, without being limited, for example, gadolinium (III) (Gd (III)), yttrium-88 ($^{88}$Y), indium-111 ($^{111}$In), and a complex of one of these and a ligand such as diethylenetriamine pentaacetic acid (DTPA), tetraazacyclododecane-1,4,7,10-tetraacetic acid (DOTA), (1,2-ethanediyldinitrilo) tetraacetic acid (EDTA), ethylendiamine, 2,2'-bipyridine (bipy), 1,10-phenanthroline (phen), 1,2-bis(diphenylphosphino)ethane (DPPE), 2,4-pentanedione (acac) or oxalate (ox), and superparamagnetic iron oxide (SPIO) and manganese oxide (MnO) may be used.

Labels suitable for the detection with a radioisotope examination device include, for example, various radioisotopes or compounds comprising one or more radioisotopes, for example, a complex of one or more radioisotopes. As radioisotopes, without being limited, for example, technetium-99m ($^{99m}$Tc), indium-111 ($^{111}$In), iodine-123 ($^{123}$I), iodine-124 ($^{124}$I), iodine-125 ($^{125}$I), iodine-131 ($^{131}$I), thallium-201 ($^{201}$Tl), carbon-11 ($^{11}$C), nitrogen-13 ($^{13}$N), oxygen-15 ($^{15}$O), fluorine-18 ($^{18}$F), copper-64 ($^{64}$Cu), gallium-67 ($^{67}$Ga), krypton-81m ($^{81m}$Kr), xenon-133 ($^{133}$Xe), strontium-89 ($^{89}$Sr), yttrium-90 ($^{90}$Y) and the like may be used. Compounds comprising radioisotopes include, without being limited, such as, for example, $^{123}$I-IMP, $^{99m}$Tc-HMPAO, $^{99m}$Tc-ECD, $^{99m}$Tc-MDP, $^{99m}$Tc-tetrofosmin, $^{99m}$Tc-MIBI, $^{99m}$TcO$_4^-$, $^{99m}$Tc-MAA, $^{99m}$Tc-MAG3, $^{99m}$Tc-DTPA, $^{99m}$Tc-DMSA, and $^{18}$F-FDG.

Labels suitable for the detection with an ultrasonic examination device include, without being limited, for example, a biocompatible gas or a substance which generates a gas under physiological condition, fatty acids, or a substance comprising these substances. A gas includes, without being limited, such as, for example, air, noble gases, nitrogen, $N_2O$, oxygen, carbon dioxide, hydrogen, inert noble gases (e.g., helium, argon, xenon and krypton), sulfur fluoride (e.g., sulfur hexafluoride, disulfur decafluoride, trifluoromethyl sulfur pentafluoride), selenium hexafluoride, halogenated silane (e.g., tetramethyl silane), low molecular weight hydrocarbon (such as e.g., $C_{1-7}$ alkane (such as methane, ethane, propane, butane and pentane), cycloalkane (such as cyclobutane and cyclopentane), alkene (such as ethylene, propene and butene)), fluorine-containing gases and ammonia; a substance which generates a gas under physiological condition include, without being limited, such as, for example, dodecafluoropentane (DDFP), a perfluorocarbon which vaporizes under physiological condition (JP A 2010-138137); and a substance comprising said substance includes such as a nanoparticle or liposome comprising said substance. Fluorine-containing gases include, without being limited, such as, for example, halogenated hydrocarbon gases (e.g., bromochlorodifluoromethane, chlorodifluoromethane, dichlorodifluoromethane, bromotrifluoromethane, chlorotrifluoromethane, chloropentafluoroethane, dichlorotetrafluoroethane and perfluorocarbon), fluorinated ketones (e.g., perfluoroacetone) and fluorinated ethers (e.g., perfluorodiethylether).

A perfluorocarbon includes, without being limited, such as, for example, perfluoroalkane (e.g., perfluoromethane, perfluoroethane, perfluoropropane, perfluorobutane, perfluoro-n-butane, perfluoropentane, perfluorohexane and perfluoroheptane), perfluoroalkene (e.g., perfluoropropene, perfluorobutene (e.g., perfluorobut-2-ene) and perfluorobutadiene), perfluoroalkyne (e.g., perfluorobut-2-yne), and perfluorocycloalkane (e.g., perfluorocyclobutane, perfluoromethylcyclobutane, perfluorodimethylcyclobutane, perfluorotrimethylcyclobutane, perfluorocyclopentane, perfluoromethylcyclopentane, perfluorodimethylcyclopentane, perfluorocyclohexane, perfluoromethylcyclohexane and perfluorocycloheptane).

As a label suitable for the detection with an ultrasonic examination device, those which have already been commercially available may be utilized. Commercially available labels for the ultrasonic examination include, without being limited, such as, for example, the 1st generation Albunex (Mallinckrodt), Echovist (SHU 454, Schering), Levovist (SHU 508, Schering), Myomap (Quadrant), Quantison (Quadrant), Sonavist (Schering) and Sonazoid (GE Healthcare), the 2nd generation Definity/luminity (Bristol-Myers Squibb Medical Imaging), Imagent-imavist (Alliance), Optison (GE Healthcare), biSphere/cardiosphere (POINT Biomedical), SonoVue (BR1, Bracco) and A1700/imagify (Acusphere), and the 3rd generation Echogen (Sonus Pharmaceuticals) (Reddy et al., World J Gastroenterol. 2011 Jan. 7; 17(1):42-8). Labels suitable for the detection with an ultrasonic examination device are also described, in addition to those described above, in JP A H5-194278, JP A H 8-310971, JP A H8-151335, JP A 2002-308802, WO 2004/069284 and WO 2005/120587.

The label contained in the functional moiety of the complex of the present invention is not particularly limited and can be selected from any of the aforementioned labels. Furthermore, the drug contained in the functional moiety of the complex of the present invention may be labeled by any of the aforementioned labels. The carrier contained in the functional moiety of the complex of the present invention can also be selected from any of the aforementioned carriers. The carrier may carry one or more aforementioned drugs and/or labels.

The drug, label and/or carrier contained in the functional moiety of the complex of the present invention may be modified to be suitable for biding to the binding moiety to an extent at which its function is not lost. Modifications compatible with the chemical binding to a given substance are well known in the art. Non-limiting examples of such modifications include such as, for example, modifications for forming a disulfide bond (e.g., thiolation), modifications for click chemistry (e.g., azidation, alkynylation), modifications for forming an avidin-biotin bond (e.g., avidinylation, biotinylation).

The functional moiety may comprise a single label, drug or carrier, or may comprise more than one labels, drugs or carriers, or a combination thereof. When the functional moiety comprises more than one labels, drugs or carriers, they may be the same or different. Moreover, a single targeting moiety may be bound to the functional moiety via a single binding moiety, or more than one targeting moiety may be bound to the functional moiety via a single or more than one binding moieties. When the functional moiety is bound to more than one binding moieties and/or targeting moieties, said binding moieties and/or targeting moieties may be the same or different.

In one embodiment, the complex of the present invention is in a form of a compound. Non-limiting examples of the complex of the present invention in a form of a compound include, for example, those in which a targeting molecule has been bound to a labeling compound or therapeutic compound, or those in which a targeting molecule has been bound to a carrier compound (e.g., a polymer) to which a labeling compound and/or a therapeutic compound has been bound via a linker (or without linker). In another embodiment, the complex of the present invention is in a form of a composition. Non-limiting examples of the complex of the present invention in a form of a composition include, for example, those in which a targeting molecule has been bound to a carrier composition (e.g., a liposome) to which a labeling compound or a therapeutic compound has been bound via a linker (or without linker).

Another aspect of the present invention relates to a composition comprising an ingredient selected from the group consisting of the targeting molecule, targeting agent, targeting carrier and complex of the present invention. The composition of the present invention may comprise, adding to the targeting molecule, targeting agent, targeting carrier and/or complex of the present invention, additional ingredients, for example, ingredients suitable for its use (e.g., an active ingredient such as a drug, a label, an additive such as an excipient). The composition of the present invention may be a pharmaceutical composition to be used in the treatment of a disease. The pharmaceutical composition of the present invention may comprise one or more pharmaceutically acceptable additives (e.g., a surfactant, carrier, diluent or excipient). Pharmaceutically acceptable additives are well known in the art of medicine and described, for example, in Remington's Pharmaceutical Sciences, 18th Ed., Mack Publishing Co., Easton, Pa. (1990), which is incorporated herein in its entity.

The complex and composition of the present invention is capable of delivering drugs etc., to a target cell selected from the group consisting of a stellate cell, a myofibroblast, a cancer-associated fibroblast, a tumor cell and an STRA6-expressing cell or the vicinity thereof. Therefore, it can be used for the treatment of a disease associated with said target cell, for example, fibrosis or a neoplastic disease. When it is used for such usage, the complex and composition of the present invention comprise a drug that treats said disease, for example, a drug that suppresses the activity or proliferation of the target cell. The complex and composition of the present invention used for such usage may sometimes be referred to as a compound for treatment or a treating agent (or a composition for treatment).

The "treatment" herein encompasses all kinds of medically acceptable preventive and/or therapeutic intervention which is aimed for the cure, temporary amelioration or prevention of a disease. For instance, the "treatment" herein encompasses medically acceptable intervention of various objects including delaying or terminating the progress of the disease associated with the target cell, involuting or eliminating a lesion, or preventing the development or recurrence of said disease.

Accordingly, the compound for treatment or treating agent of the present invention comprises a compound for treatment or treating agent (or a composition for treatment) for treating a disease associated with the target cell, and a compound for prevention or preventing agent (or a composition for prevention) for preventing a disease associated with the target cell.

Diseases associated with stellate cells include, without being limited, such as, for example, fibrosis such as hepatic fibrosis, hepatic cirrhosis, pancreatic fibrosis, vocal cord scarring, vocal cord mucosa fibrosis and laryngeal fibrillization (see, Patent Literature 1).

Diseases associated with myofibroblast include, without being limited, such as, for example, fibrosis of various organs such as hepatic fibrosis, hepatic cirrhosis, vocal cord scarring, vocal cord mucosa fibrosis, laryngeal fibrillization, lung fibrosis, pancreatic fibrosis, bone marrow fibrosis, myocardial infarction, myocardial fibrillization after myocardial infarction, myocardial fibrosis, endomyocardial fibrosis, splenic fibrosis, mediastinal fibrosis, sublingual mucosa fibrosis, fibrillization of the intestinal tract (e.g., those associated with an inflammatory bowel disease), retroperitoneal fibrosis, uterus fibrosis, scleroderma and mammary fibrosis.

Diseases associated with cancer-associated fibroblasts include, without being limited, such as, for example, solid tumors such as brain tumor, head and neck cancer, breast cancer, lung cancer, esophageal cancer, gastric cancer, duodenal cancer, appendiceal cancer, colorectal cancer, rectal cancer, hepatic cancer, pancreatic cancer, gallbladder cancer, bile duct cancer, anal cancer, renal cancer, ureteral cancer, bladder cancer, prostate cancer, penile cancer, testicular cancer, uterine cancer, ovarian cancer, vulvar cancer, vaginal cancer, skin cancer, fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma and osteosarcoma.

Diseases associated with tumor cells include, without being limited, such as, for example, neoplastic diseases such as any benign tumors and malignant tumors of any parts of body, for example, brain, head and neck, chest, limbs, lung, heart, thymus, esophagus, stomach, small intestine (duodenum, jejunum, ileum), large intestine (colon, cecum, appendix, rectum), liver, pancreas, gallbladder, anal, kidney, urinary duct, bladder, prostate, penis, testis, uterus, ovary, vulva, vagina, skin, striated muscle, smooth muscle, synovial membrane, cartilage, bone, thyroid, adrenal gland, peritoneum, mesenterium, bone marrow, blood, vascular system, lymphatic system such as lymph nodes. Non-limiting examples of malignant tumors include sarcomas such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma and osteosarcoma, carcinomas such as brain tumor, head and neck cancer, breast cancer, lung cancer, esophageal cancer, gastric cancer, duodenal cancer, appendiceal cancer, colorectal cancer, rectal cancer, hepatic cancer, pancreatic cancer, gallbladder cancer, bile duct cancer, anal cancer, renal cancer, ureteral cancer, bladder cancer, prostate cancer, penile cancer, testicular cancer, uterine cancer, ovarian cancer, vulvar cancer, vaginal cancer and skin cancer, and furthermore leukemia and malignant lymphoma.

Diseases associated with STRA6-expressing cells include, apart from the diseases described above associated with tumor cells, diseases associated with cells selected from the group consisting of RPE cells, Sertoli cells, astrocytes, for example, retinitis pigmentosa, age-related macular degeneration, Sertoli cell tumor and astrocytoma.

The complex and composition of the present invention may be for controlling (e.g., suppressing, maintaining or promoting) the activity or proliferation of a target cell selected from the group consisting of a stellate cell, a myofibroblast, a cancer-associated fibroblast, a tumor cell and an STRA6-expressing cell, and in that case, they include drugs which suppress the activity or proliferation of the target cell.

The targeting molecule, targeting agent, targeting carrier, complex and composition of the present invention may be for delivering a substance to a target cell selected from the group consisting of a stellate cell, a myofibroblast, a cancer-associated fibroblast, a tumor cell and an STRA6-expressing cell. The substance to be delivered is not particularly limited and includes, for example, substances to be delivered which can be carried by aforementioned targeting carrier of the present invention, or aforementioned drug or label described herein which is contained in the functional moiety of the complex of the present invention. The delivery of the substance may be carried out in vitro or in vivo.

The complex and composition of the present invention is capable of delivering a label to a target cell selected from the group consisting of a stellate cell, a myofibroblast, a cancer-associated fibroblast, a tumor cell and an STRA6-expressing cell. Therefore it can be used for labeling the target cell or a tissue comprising the same. The complex and the composition of the present invention used for such usage may sometimes be referred to as a compound for labeling or a labeling agent (or a composition for labeling). The compound for labeling or the labeling agent of the present invention comprises a label. Non-limiting examples of the label comprises those described above. The compound for labeling or the labeling agent of the present invention can be used for detecting or imaging the target cell or tissue comprising the same described above. The labeling agent of the present invention used for such usage may sometimes be referred to as a compound for detecting or a detecting agent (or a composition for detecting), or a compound for imaging or an imaging agent (or a composition for imaging).

The labeling, detection or imaging of a cell or tissue may be carried out in vitro or in vivo. The detection or imaging of a cell or tissue may also be carried out non-destructively, preferably non-invasively. Here, "non-invasively" means that the detection or imaging will not destruct the tissue of interest; for instance, when the tissue of interest is liver, the detection or imaging includes exposing the liver by open surgery or obtaining images of liver surface by endoscopy, but not incising the liver and exploring inside of it. Moreover, "non-invasively" means that the detection of the label contained in the detecting agent or imaging agent is carried out without intentionally damaging the organism, and typically includes the detection outside the organism, though it also includes the detection by inserting a detector such as an endoscope or ultrasonic prove through a natural aperture such as the oral cavity, nasal cavity, anal, urethra, auditory canal or vagina.

The compound for labeling or labeling agent of the present invention can be used for examination or diagnosis of a disease associated with the target cell. For instance, a stellate cell or a myofibroblast is known to proliferate in the lesion of fibrosis, so that a high level of a label being detected in a tissue indicates a large population of stellate cells or myofibroblasts being present in the tissue, providing an index of fibrosis affecting that tissue (see, e.g., Patent Literature 7). On the other hand, because a cancer-associated fibroblast or a tumor cell is localized in a cancer or tumor tissue, a high level of a label being detected in particular part of the body of the subject is an index of the presence of a cancer or tumor in that part. The compound for labeling or the labeling agent of the present invention may sometimes be particularly referred to as a compound for examining or an examining agent (or a composition for examination), or a compound for diagnosing or a diagnosing agent (or a composition for diagnosing). Here, an examination of a disease includes, for example, comparing the measured index (e.g., the signal intensity from the labeling agent) with predetermined standard (e.g., predetermined cut-off value) and presenting the examination result (e.g., a positive or negative result of the examination) about the disease based on the comparison, but not identifying the disease. Therefore, a judgement by a medical doctor is not necessary for the examination of the disease. On the other hand, a diagnosis of a disease includes the identification of the disease by a medical doctor based on various information.

The compound for labeling or labeling agent of the present invention can also be used for monitoring a disease associated with the target cell. The compound for labeling or the labeling agent of the present invention used for such usage may sometimes be particularly referred to as a compound for monitoring or a monitoring agent (or a composition for monitoring). Here, the monitoring of a disease means to monitor over time a transition of a disease in certain subject, for example, a remission, exacerbation or persistence, etc. of the disease.

The compound for detecting, the detecting agent, the compound for imaging and the imaging agent of the present invention can be used for the examination, diagnosis or monitoring of certain disease, when a target cell exhibits a characteristic behavior in said disease, for example, without being limited, when the target cell abnormally proliferates in said disease. Such disease includes a disease associated with the target cell. Therefore, the compound for detecting, the detecting agent, the compound for imaging and the imaging agent of the present invention may constitute one embodiment of the compound for detecting, the detecting agent, a compound for diagnosing, a diagnosing agent, a compound for monitoring or a monitoring agent of the present invention.

The compound for labeling or labeling agent of the present invention can also be used for assessing the effect of a treatment on a disease associated with a target cell. The compound for labeling or the labeling agent of the present invention used for such usage may sometimes be particularly referred to as a compound for assessment or an assessing agent (or a composition for assessment).

The complex and composition of the present invention may be administered via various route including oral and parenteral routes, for example, without limitation, oral, intravenous, intramuscular, subcutaneous, topical, rectal, intra-arterial, intraportal, intraventricular, transmucosal, percutaneous, intranasal, intraperitoneal, intrapulmonary and intrauterine routes, and may be formulated in a dosage form suitable for each administration route. Any known dosage forms and formulating methods may be employed as appropriate (see, e.g., "Standard Pharmaceutics [HYOJUN YAKUZAIGAKU]", Watanabe, Yoshiteru et al. eds., Nankodo Co., Ltd., 2003; and Remington's Pharmaceutical Sciences, 18th Ed., Mack Publishing Co., Easton, Pa. (1990)).

For instance, dosage forms suitable for oral administration include such as, without limitation, powders, granules, tablets, capsules, liquids, suspensions, emulsions, gels and syrups. Dosage forms suitable for parenteral administration include injections such as injectable solutions, injectable suspensions, injectable emulsions, and injections prepared when needed. Formulations for parenteral administration may be in a form of an aquatic or non-aquatic isotonic sterile solution or suspension.

The complex and composition of the present invention may be provided in any form. In view of storage stability, it may be provided in a form that is capable of being prepared when needed, for example, in a form that is capable of being prepared by a medical doctor and/or a pharmacist, a nurse or other paramedical in a medical scene or vicinity thereof. In this case, the complex and composition of the present invention are provided as one or more containers comprising at least one of their essential constituents, and are prepared before use, for example, within 24 hours, preferably within 3 hours, and more preferably immediately before use. For preparation, reagents, solvents, dispensing apparatuses normally available at the place of preparation may be used as appropriate.

Further aspect of the present invention relates to a kit or pack comprising the targeting carrier, complex or composition of the present invention or the constituents thereof, for preparing the targeting carrier, complex and composition of the present invention, for delivering a substance to a target cell, for controlling the activity or proliferation of the target cell, for treating, examining, diagnosing or monitoring a disease associated with the target cell, for labeling, detecting or imaging the target cell or a tissue comprising the same, or for assessing the effect of the treatment for the disease associated with the target cell, and to the targeting carrier, complex or composition of the present invention or the constituents thereof provided in a form of such a kit or pack.

Each constituent of the targeting carrier, complex or composition of the present invention contained in the kit or pack of the present invention is as described above for the targeting carrier, complex or composition of the present invention. The kit may further comprise, adding to those describe above, an instruction for methods for preparing or using (e.g., the method for administration) of the targeting carrier, complex or composition of the present invention, for example, a written instruction for use or a medium recording the information about the method for use, for example, a flexible disk, CD, DVD, Blue-ray disk, memory card, USB memory stick, and the like. Furthermore, although the kit or pack of the present invention may comprise all of the constituents for constituting completely the targeting carrier, complex or composition of the present invention, the kit or pack may not necessarily comprise all of the constituents. Therefore, the kit or pack of the present invention may not comprise reagents or solvent which are normally available at a medical scene or experimental facility, for example, sterilized water, physiological saline, glucose solution, and the like.

Another aspect of the present invention relates to a method for controlling the activity or proliferation of a target cell selected from the group consisting of a stellate cell, a myofibroblast, a cancer-associated fibroblast, a tumor cell and an STRA6-expressing cell, wherein the method comprises a step of administrating an effective amount of the complex or composition of the present invention comprising a drug that controls the activity or proliferation of said target cell to a subject or cell or tissue in need thereof. Here, controlling the activity or proliferation of the target cell includes the suppression, maintenance and promotion of the activity or proliferation. Therefore, an effective amount in the method above is, for example, an amount which suppresses, maintains or promotes the activity or proliferation of the target cell. The maintenance of the activity or proliferation of the target cell includes maintaining the activity or proliferation at the initial state under the condition in which the activity or proliferation of the target cell is suppressed or promoted over time. The cell or tissue to which the complex or composition of the present invention is administered typically comprises the target cell and may be present inside or outside of the organism. Therefore, the method above which comprises a step of administrating the complex or composition of the present invention to a cell or tissue encompasses those carried out in vitro, ex vivo or in vivo.

Another aspect of the present invention relates to a method of treating a disease associated with a target cell selected from the group consisting of a stellate cell, a myofibroblast, a cancer-associated fibroblast, a tumor cell and an STRA6-expressing cell, wherein the method comprises a step of administrating an effective amount of the complex or composition of the present invention comprising a drug that treats said disease to a subject in need thereof. Here, an effective amount is, for example, an amount that prevents the development and recurrence of said disease, or an amount that cures said disease. Diseases associated with the target cell and drugs that treat said diseases are as described above for the compound for treatment and treating agent of the present invention.

Another aspect of the present invention relates to a method of labeling, detecting or imaging a target cell selected from the group consisting of a stellate cell, a myofibroblast, a cancer-associated fibroblast, a tumor cell and an STRA6-expressing cell or a tissue comprising the same, wherein the method comprises a step of administrating an effective amount of the complex or composition of the present invention comprising a label to a subject or cell or tissue in need thereof. Here, an effective amount is, for example, an amount that is capable of detectably labeling the target cell or target tissue. As the label in said method, for example, those described herein may be used. The cells or tissue to which the complex or composition of the present invention is administered may include the target cell, and may be present inside or outside of the organism. Therefore, the methods described above which comprise administrating the complex or composition of the present invention to the cell or tissue include those performed in vitro, ex vivo or in vivo.

Another aspect of the present invention relates to a method of examining, diagnosing or monitoring a disease associated with a target cell selected from the group consisting of a stellate cell, a myofibroblast, a cancer-associated fibroblast, a tumor cell and an STRA6-expressing cell, wherein the method comprises a step of administrating an effective amount of the complex or composition of the present invention comprising a label to a subject in need thereof. Here, an effective amount is, for example, an amount that is capable of detectably labeling the target cell or target tissue. As the label in said method, for example, those described herein may be used. Diseases associated with the target cell are as described above for the compound for treatment and treating agent of the present invention. When the target cell exhibits a characteristic behavior in the disease, for example, without being limited, when the target cell abnormally proliferates in certain disease, the examination, diagnosis or monitoring of the disease associated with the target cell may also be carried out by detecting or imaging the target cell with an effective amount of the complex or composition of the present invention comprising a label.

Another aspect of the present invention relates to a method of assessing the effect of treatment for a disease associated with a target cell selected from the group consisting of a stellate cell, a myofibroblast, a cancer-associated fibroblast, a tumor cell and an STRA6-expressing cell, wherein the method comprises a step pf administrating an effective amount of the complex or composition of the present invention comprising a label to a subject in need thereof. Here, an effective amount is, for example, an amount that is capable of detectably labeling the target cell or target tissue. As the label in said method, for example, those described herein may be used. Diseases associated with the target cell are as described above for the compound for treatment and treating agent of the present invention.

Another aspect of the present invention relates to a method of delivering a substance to a target cell selected from the group consisting of a stellate cell, a myofibroblast, a cancer-associated fibroblast, a tumor cell and an STRA6-expressing cell, wherein the method comprises a step of targeting the substance with a targeting molecule, a targeting agent or a targeting carrier of the present invention, and a step of administrating the targeted substance to a subject or a medium comprising a target cell. The substance to be delivered is not particularly limited and includes such as, for example, a label, a drug, a carrier which may comprise a label and/or drug. The method of delivery of the present invention includes those performed in vitro, ex vivo or in vivo.

The effective amount of the complex or composition of the present invention in each of the methods of the present invention is preferably an amount that does not cause an adverse effect exceeding over the benefit from its administration. The effective amount of the complex or composition of the present invention in each of the methods of the present invention may be determined as appropriate based on in vitro test using cultured cells, etc., or a test in an experimental animal such as a mouse, rat, dog or pig, or an animal model of the disease. Such testing methods are well known to a person skilled in the art.

The specific amount of the complex or composition administered to a subject in the method of the present invention may be determined in consideration of various conditions associated with the subject in need of the administration such as, for example, the type of the target, the aim of the method, the content of the therapy, the type of the disease, the severity of the symptom, general health conditions, age, body weight, sex and diet of the subject, time and frequency of the administration, concurrent medication, responsiveness to the therapy, and compliance to the therapy. Dairy total dosage of the complex or composition of the present invention may be, without being limited, for example, from about 1 µg/kg to about 1000 mg/kg body weight, from about 10 µg/kg to about 100 mg/kg body weight, or from about 100 µg/kg to about 10 mg/kg body weight. Alternatively, the dosage may be calculated based on the surface area of the patient.

Routes of administration include various routes including both oral and parenteral routes such as, for example, oral, intravenous, intramuscular, subcutaneous, topical, rectal, intra-arterial, intraportal, intraventricular, transmucosal, transdermal, intranasal, intraperitoneal, intrapulmonary and intrauterine routes.

The frequency of administration varies depending of the nature of the formulation or composition used or conditions of the subject as above, though it may be, for example, multiple times a day (i.e., 2, 3, 4, 5 or more times a day), once a day, once in several days (i.e., once in 2, 3, 4, 5, 6, 7 days, etc.) several times a week (e.g., 2, 3 or 4 times a week), once a week, or once in several weeks (i.e., every 2, 3 or 4 weeks).

The labeling, detecting, imaging, examining, diagnosing, monitoring and/or assessing method of the present invention may further comprise detecting a label contained in the complex or composition of the present invention comprising the label. The label may be contained in the complex or composition at the time of detection, or may be present separately from the complex or composition. The detection of the label can be carried out by any techniques which can detect the label, for example, without limitation, by a technique using a macroscopic, optical examination device (e.g., an optical microscope, a fluorescent microscope, a phase-contrast microscope, and an in vivo imaging device), an X-ray device (e.g., a plain X-ray device or CT (computed tomography) device), an MRI (magnetic resonance imaging) device, a radioisotope examination device (e.g., a scintigraphic, PET or SPECT device), an ultrasonic examination device and a thermography device. Labels suitable for each detecting technique are known to a person skilled in the art (see, e.g., Lecchi et al., 2007, supra), and non-limiting examples has already been described above.

In one embodiment, the target cell is detected or imaged in vivo. For such detection or imaging, any devices suitable for in vivo detection may be used, such as, without limitation, an optical examination device (e.g., an in vivo imaging device), an X-ray device (e.g., a plain X-ray device or CT (computed tomography) device), an MRI (magnetic resonance imaging) device, a radioisotope examination device (a scintigraphic, PET or SPECT device), an ultrasonic examination device and a thermography device, and labels suitable for such detection are also known to a person skilled in the art (see, e.g., Lecchi et al., 2007, supra).

By detecting or imaging the target cell in vivo, the localization of the target cell (e.g., an organ and apparatus) or the lesion of the disease associated with the target cell can be determined. Therefore, the present invention also relates to a method of determining the localization of the target cell and/or the lesion of the disease associated with the target cell, the method comprising administering an effective amount of the complex or composition of the present invention comprising a label to a subject in need thereof. Such method is useful for diagnosing the disease associated with the target cell.

Furthermore, detecting or imaging the target cell in vitro or in vivo may provide information useful for for diagnosing the disease associated with the target cell, such as the number or distribution of the target cell. Therefore, the present invention also relates to a method for assisting the diagnosis of a disease associated with the target cell, the method comprising administering an effective amount of the complex or composition of the present invention comprising a label. The method may further comprise providing a medical doctor with information useful for for diagnosing the disease associated with the target cell.

The methods of examining and diagnosing the disease associated with the target cell and the method for assisting the diagnosis of a disease associated with the target cell of the present invention may further comprise a step of comparing the result of label detection in the subject with the reference result of label detection. The reference result of the detection may be, for example, the result of label detection in a subject who has been known not to have the disease associated with the target cell (also referred to as a "negative subject"), which is also referred to as a "negative reference", or the result of label detection in a subject who has been known to have the disease associated with the target cell (also referred to as a "positive subject"), which is also referred to as a "positive reference". The reference result of label detection may be a mean or median of the detection result in more than one negative or positive subjects.

Accordingly, the method of examining the disease associated with the target cell of the present invention may further comprise, for example, a step of presenting the negative result of the detection when the result of label detection in the subject was equal to (e.g., not significantly different from) the negative reference, and/or a step of presenting the positive result of the detection when the result of label detection in the subject was significantly greater than the negative reference, and/or a step of presenting the positive result of the detection when the result of label detection in the subject was equal to (e.g., not significantly different from) the positive reference.

The result of label detection in the detecting, imaging, examining, diagnosing, monitoring and/or assessing methods of the present invention may be a signal intensity and/or signal distribution of detected label.

A signal intensity of a label means an intensity or analogous measurement of various signals generated from the label, for example, a fluorescent signal, luminescent signal, magnetic signal or radioactive signal, and is typically measured by appropriate means for detection. Specific examples of the means for detection is as already described above. The signal intensity may be obtained from whole subject or may be obtained from certain part or area of the subject. Moreover, the signal intensity may be a mean value against the area or volume of the measured part, or an integrated value. When the signal intensity varies over time, the signal intensity in the present method may be of certain time point, or may be those integrated for certain time period. When the number or activity of the target cells increases with the progression of the disease, an increase in the signal intensity can be an index of the presence or progression of the disease, whereas, on the contrary, a decrease in the signal intensity can be an index of an improvement in the disease.

The signal distribution of the label means information associated with location of the signal generated from the label in the subject, which may be two-dimensional or three-dimensional. Collating the signal distribution with anatomical positional relation of organs or structural information of the tissue such as a CT image, an MRI image or an ultrasonogram can identify the tissue from which the signal is generated. When the signal varies over time, the signal distribution in the present method may be of certain time point, or may be those integrated for certain time period. When the area of the presence of the target cells is expanded with the progression of the disease, the expansion of the signal distribution can be an index of the presence or progression of the disease, whereas, on the contrary, a decrease in the signal distribution can be an index of an improvement in the disease.

In the methods of the present invention, the signal intensity and distribution may be assessed in combination. Assessment of the location and intensity of the detected signal can provide more precise determination and more accurate information.

The monitoring method of the present invention may further comprise comparing the result of label detection at the first time point with that of the second time point which is after the first point. For instance, when the detection result is an index of the number of the target cells (e.g., the signal intensity or signal distribution from the label taken up by the target cells), a smaller index at the second time point than the index at the first time point indicates a decrease in the number of the target cells; when the disease associated with the target cell is exacerbated by the proliferation of the target cell, a smaller index at the second time point than the index at the first time point means an improvement in said disease. For instance, a result of an improvement in the disease can be presented if the signal intensity at the second time point is lower than that at the first time point, whereas, on the contrary, a result of an exacerbation of the disease can be presented if the signal intensity at the second time point is higher than that at the first time point. Moreover, for example, a result of an improvement in the disease can be presented if the signal distribution at the second time point is decreased as compared with that at the first time point, whereas, on the contrary, a result of an exacerbation of the disease can be presented if the signal distribution at the second time point is expanded as compared with that at the first time point.

The assessing method of the present invention may further comprise comparing the result of label detection at the first time point before treatment with the result of label detection at the second time point after treatment after the first time point, or comparing the result of label detection at the first time point after the first treatment with the result of label detection at the second time point after the second treatment which was carried out after the first treatment. For instance, when the detection result is an index of the number of the target cells (e.g., the signal intensity or signal distribution from the label taken up by the target cells), a smaller index at the second time point than the index at the first time point indicates a decrease in the number of the target cells; when the disease associated with the target cell is exacerbated by the proliferation of the target cell, a smaller index at the second time point than the index at the first time point means an improvement in said disease, namely a positive effect by the treatment. For instance, the disease has been improved by the treatment if the signal intensity at the second time point is lower than that at the first time point, and therefore a result can be presented that the treatment has been successful. On the contrary, if the signal intensity at the second time point is higher than that at the first time point, the disease was worsened by the treatment, and a result can be presented that either the treatment was not very successful or it was unsuccessful. Furthermore, for example, the disease has been improved by the treatment if the signal distribution at the second time point is decreased as compared with that at the first time point, and therefore a result can be presented that the treatment has been successful. On the contrary, if the signal distribution at the second time point is expanded as compared with that at the first time point, the disease was worsened by the treatment, and a result can be presented that either the treatment was not very successful or it was unsuccessful.

Herein, the term "subject" means an individual of any living organisms, preferably an animal, more preferably a mammal, further preferably a human individual. In the present invention, the subject may be healthy (e.g., without certain or any disease) or may be suffering from a disease. However, in cases where the treatment, examination, diagnosis or monitoring of a disease associated with the target cell is contemplated, the subject typically means a subject who is suffering or at a risk of suffering from said disease; in cases where the assessment of a treatment against a disease associated with the target cell is contemplated, the subject typically means a subject who is undergoing or about to undergo a therapy against said disease.

EXAMPLES

In the following examples, the present invention will be explained in more details. These examples are aimed at demonstrating the present invention but not limiting the scope of the present invention.

Example 1: Preparing a Targeting Molecule-Carrier Complex

Following peptides were prepared as targeting molecules:

TABLE 1

| Peptide name | Sequence | SEQ ID NO |
|---|---|---|
| RBP Loop 1 | AKKDPEGLFLQDNI | 3 |
| No. 10 | KDPEGLFLQD | 6 |
| No. 10-1 | AKKDPEGLFLQDN | 7 |
| No. 10-2 | AKKDPEGLFLQD | 8 |
| No. 10-3 | KKDPEGLFLQDNI | 9 |
| No. 10-4 | KDPEGLFLQDNI | 10 |
| No. 10-5 | KKDPEGLFLQD | 11 |
| No. 10-6 | KDPEGLFLQDN | 12 |
| No. 10-7 | KKDPEGLFLQDN | 13 |
| R B P Loop 2 | AKGRVRLLNNWDVCA | 4 |
| R B P Loop 3 | KYWGVASFLQKGNDD | 5 |

All of the peptide above were obtained from Sigma-Genosys. As a positive control, vitamin A (all-trans-retinol, Sigma Aldrich) was prepared. Vitamin A was dissolved in DMSO at a concentration of 10 mM to prepare a stock solution and cryopreserved till it is used. As the carrier to which the targeting molecule is bound, LipoTrust™ SR (Hokkaido System Science Co., Ltd.) comprising a liposome-forming cationic lipid DC-6-14 was prepared, and as the drug to be carried by the carrier, an siRNA against HSP47 (HSP47 C, Hokkaido System Science Co., Ltd.) was prepared. The sequences of the siRNA is shown below (in the sequences, small letters expresses RNAs and capital letters expresses DNAs, respectively):

```
The sense strand:
                              (SEQ ID NO: 14)
5' ggacaggccucuacaacuaTT 3'

The antisense strand:
                              (SEQ ID NO: 15)
5' uaguuguagaggccuguccTT 3'
```

The siRNA was dissolved in nuclease-free water (Ambion, Cat. No. AM9937) at a concentration of 10 mg/ml to prepare a stock solution and cryopreserved till it is used.

LipoTrust™ SR was dissolved in nuclease-free water (Ambion, Cat. No. AM9937) at a concentration of 1 mM of the cationic lipid. 10 µl of this liposome solution was placed in an Eppendorf tube, to which added 1 µl of the stock solution of each peptide above dissolved in DMSO at predetermined concentration (1.1 mM, 1.25 mM, 2.5 mM, 3.4 mM, 5 mM or 10 mM for experiments whose results are shown in FIG. 1; 90 mM for experiments whose results are shown in FIG. 2) or the stock solution of vitamin A above, and the mixture was vortexed for 15 seconds. To this mixture, 1.5 µl of the above siRNA stock solution was added and mixed, then 17.5 µl of 5% glucose aq. solution (OTSUKA GLUCOSE INJECTION 5%, Otsuka Pharmaceutical Co., Ltd.) was added and mixed. Thus obtained solution of liposome-peptide (or vitamin A)-siRNA complex (lipoplex) was left still under shade for 15 min at room temperature. Also, a mixture of the peptide and siRNA without LipoTrust™ SR was prepared as a control.

Example 2: Introducing the siRNA to a Stellate Cell

Two days before the siRNA introduction, hepatic stellate cells (HSCs) prepared from a rat liver according to the method of Schaefer et al. (Schaefer et al., Hepatology. 1987 July-August; 7(4):680-7) were inoculated uniformly onto a 6-well plate at a density of $0.2 \times 10^5$/well and cultured in a Dulbecco's modified Eagle's medium (D-MEM, Sigma Aldrich, Cat. No. D6546, hereinbelow referred to as "culture medium") containing 10% fetal bovine serum (Thermo HyClone, Cat. No. SH30070.03), 2% L-glutamine (Sigma Aldrich, Cat. No. G7513) and 1% penicillin-streptomycin (Sigma Aldrich, Cat. No. G1146).

The culture medium was removed, 900 µl of fresh culture medium was added to each well, and then this was incubated for at least 30 minutes at 37° C. To 30 µl of each lipoplex solution obtained in Example 1, 100 µl of 5% glucose solution was added to make a mixed solution of 130 µl, and 100 µl of said mixture was added to corresponding well. The final concentration of the siRNA at this time was 11.5 µg/ml. After incubating at 37° C., in 5% $CO_2$ for 30 minutes, the medium comprising the lipoplex solution was removed and substituted with the culture medium, and this was cultured under normal condition for 24-36 hours.

Total RNA extraction of each sample was carried out using RNeasy Mini kit (Qiagen). Firstly, the culture medium was removed, and 350 µl/well each of RLT/2ME solution which was prepared in advance by mixing RLT solution attached to RNeasy Mini kit with 1% (v/v) 2-mercaptoethanol (2ME, Wako) was dispensed into each well. Total volume of the cell lysate was homogenized with QIAshredder (Qiagen), centrifuged at 4° C. and 12000 rpm for 2 min, and then total RNA was extracted according to the manufacturer's instruction. The obtained RNA was quantified using NanoDrop 2000 (Thermo Fisher Scientific), and cDNA was synthesized by RT-PCR. 20 µl total volume/tube of the reaction solution consisting of 4 µl of the reverse transcriptase mix (Super Script VILO Master Mix, Invitrogen, 11755-250) and 16 µl of total RNA of each sample (containing 100-500 ng or more RNA) was reacted at 25° C. for 5 min, at 42° C. for 60 min, then at 85° C. for 5 min, respectively, and subsequently stored at 4° C.

The suppression of HSP47 expression was analyzed by quantitative PCR. As a standard template, the untreated cell sample was used in 10-fold dilution series (the stock solution, 10- and 100-fold dilutions). To each well of MicroAmp (Optical 96-well Reaction Plate, Applied Biosystems, Cat. No. 4306737) added a 48 µl premix consisting of 22 µl of sterile water, 25 µl of Power SYBR® Green (Applied Biosystems, Cat. No. 4367669) and 1 µl of primer mix. The primer mix comprises 50 µM each of the primer set against HSP47 or GAPDH, an internal standard gene, as shown below:

Rat HSP47:
(forward primer, SEQ ID NO: 16)
5' TGACCTGCAGAAACATCTGG 3'

(reverse primer, SEQ ID NO: 17)
5' AGGAAGATGAAGGGGTGGTC 3'

GAPDH (the internal standard, common in human/rat)
(forward primer, SEQ ID NO: 18)
5' ACCATCTTCCAGGAGCGAGA 3'

(reverse primer, SEQ ID NO: 19)
5' GCATGGACTGTGGTCATGAG 3'

To the corresponding well, 2 µl of the template cDNA obtained from each sample was added to make a total volume of 50 µl. This was set in a real-time PCR device (7300 Real Time PCR System, Applied Biosystems) and reacted in the condition in the table below.

TABLE 2

| | | |
|---|---|---|
| 95° C. | 10 min | 1 cycle |
| 95° C. | 15 sec | |
| 64° C. | 30 sec | 40 cycles |
| 82° C. | 31 sec | |
| 95° C. | 15 sec | |
| 60° C. | 1 min | 1 cycle |
| 95° C. | 15 sec | |
| 60° C. | 15 sec | |

The results are shown in FIGS. 1 and 2. The graphs indicate the expression level of HSP47 relative to GAPDH in each condition, referring to the untreated cell as 100. A smaller value indicates a greater suppression of HSP47 expression, namely an efficient introduction of siRNA. The result shown in FIG. 1 indicates that there was a concentration-dependent suppression of HSP47 expression when Loop 1 and Loop 2 were used as the targeting molecules, and in particular that the suppression rate by the complex using Loop 1 as the targeting molecule was comparable to that by vitamin A. Furthermore, the results shown in FIG. 2 indicates that the suppression rate by the complexes using as targeting molecules the parts of Loop 1 comprising the peptides in which the N- and C-terminals of Loop 1 have been shortened by 1 amino acid each (peptide No. 10 and Nos. 10-1 to 10-6) were comparable to those by Loop 1 and vitamin A. The table below contains the numerical values of the results shown in FIG. 2.

TABLE 3

| Targeting molecule | HSP47 expression rate (%) | SEQ ID NO | Amino Acid (AA) Residues Correspondences |
|---|---|---|---|
| VA | 46.8 | | |
| VA (−) | 97.4 | | |
| Loop 1 | 49.0 | 3 | AA Residues 46-59 of SEQ ID NO: 2 |
| No. 10 | 57.2 | 6 | AA Residues 3-12 of SEQ ID NO: 3 |
| No. 10-1 | 39.3 | 7 | AA Residues 1-13 of SEQ ID NO: 3 |
| No. 10-2 | 48.5 | 8 | AA Residues 1-12 of SEQ ID NO: 3 |
| No. 10-3 | 31.2 | 9 | AA Residues 2-14 of SEQ ID NO: 3 |
| No. 10-4 | 42.9 | 10 | AA Residues 3-14 of SEQ ID NO: 3 |
| No. 10-5 | 40.4 | 11 | AA Residues 2-12 of SEQ ID NO: 3 |
| No. 10-6 | 44.3 | 12 | AA Residues 3-13 of SEQ ID NO: 3 |

*VA was used at the final concentration of 7.7 µM and each peptide was used at the final concentration of 69.2 µM.

The results described above indicate that the peptide comprising the sequence of the cell binding moiety of RBP is useful as the targeting molecule for delivering a drug, etc. in stellate cell-specific manner.

Example 3: Targeting by a Mutant Peptide

In order to verify that the targeting to the stellate cell by RBP Loop 1 is either due to the amino acid composition of the peptide or the amino acid sequence of the peptide, a similar experiment as Example 2 was carried out using rat hepatic stellate cells and RBP Loop 1 and the mutant peptides shown in the table below. The lipoplex comprising each peptide was prepared in a similar manner as Example 1 using 10 mM peptide stock solution in DMSO, and added to a well containing rat hepatic stellate cells such that the final concentration of the peptide was 7.7 µM and that of the siRNA was 11.5 µg/ml.

TABLE 4

| Peptide name | Sequence | SEQ ID NO |
|---|---|---|
| RBP Loop 1 (L1) | AKKDPEGLFLQDNI | 3 |
| Mutant peptide 1 (E3K6) | AKEDPKGLFLQDNI | 20 |
| Mutant peptide 2 (D3K4) | AKDKPEGLFLQDNI | 21 |
| Mutant peptide 3 (D3K12) | AKDDPEGLFLQKNI | 22 |

Mutant peptide 1 is an RBP Loop 1 in which the lysine at position 3 has been replaced with a glutamate and the glutamate at position 6 with a lysine, respectively. Mutant peptide 2 is an RBP Loop 1 in which the lysine at position 3 has been replaced with an aspartic acid, and the aspartic acid at position 4 with a lysine, respectively. Mutant peptide 3 is an RBP Loop 1 in which the lysine at position 3 has been replaced with an aspartic acid, and the aspartic acid at position 12 with a lysine, respectively. Therefore, these mutant peptides are identical to RBP Loop 1 in their amino acid composition but are different in their amino acid sequences.

From the result shown in FIG. 3, the extent of the suppression of the expression of HSP47 gene was lower in any of the groups using Mutant peptides 1, 2 and 3 as targeting molecules as compared with the group using RBP Loop 1 as the targeting molecule, suggesting that the important factor for the suppression of gene expression is rather the amino acid sequence itself of RBP Loop 1 than its amino acid composition.

Example 4: Targeting by Peptide Mimetics

In order to verify whether a peptide mimetic of the cell binding moiety of RBP could act as the targeting molecule for the stellate cell, a similar experiment as Example 2 was carried out using rat hepatic stellate cells, and a retro-inverso peptide of RBP Loop 1 (RI:d-INDQLFLGEPDKKA-amide (SEQ ID NO: 26) (a peptide which is constituted by D-amino acids having an opposite sequence to SEQ ID NO: 3)) as a peptide mimetic, and RBP Loop 1 (L1:SEQ ID NO: 3) as a control peptide. The lipoplex comprising each peptide was prepared in a similar manner as Example 1 using 30 mM peptide stock solution in DMSO, and added to wells comprising rat hepatic stellate cells such that the final concentration of the peptide was 23.1 µM and the final concentration of the siRNA was 11.5 µg/ml.

From the result shown in FIG. 4, it is understood that the retro-inverso peptide has almost the same targetability as that of RBP Loop 1. Because the retro-inverso peptide has an analogous spatial conformation (topology) of said chains as parent peptide, this result indicates that a peptide mimetic having a similar side chain topology as a peptide that acts as the targeting molecule to a stellate cell such as those described in Examples 1 to 3 would also act as the targeting molecule to the stellate cell.

Example 5: Targeting by a Scrambled Peptide

In order to confirm that the targeting by RBP Loop 1 to a stellate cell does not depends on the amino acid composition of the peptide but on the amino acid sequence of the peptide, a similar experiment as Example 2 was carried out using rat hepatic stellate cells, and RBP Loop 1 (L1: SEQ ID NO: 3) as the test peptide and a scrambled peptide having the same amino acid composition with the test peptide and a different amino acid sequence from it (scr:AKFQKLEPGDDLNI, SEQ ID NO: 23). The lipoplex comprising each peptide was prepared in a similar manner as Example 1 using 10 mM peptide stock solution in DMSO, and added to wells comprising rat stellate cells such that the final concentration of the peptide was 7.7 µM and the final concentration of the siRNA was 11.5 µg/ml. From the results shown in FIG. 5, the expression rate of HSP47 gene was significantly decreased in the group using RBP Loop 1 as the targeting molecule, whereas the result in the group using the scrambled peptide as the targeting molecule was almost the same as the result in the group using no targeting molecule (VA(−)), suggesting that the important factor for the targeting is rather the amino acid sequence itself of RBP Loop 1 than its amino acid composition.

Example 6: Targeting to a Cancer Cell

In order to verify whether the peptide of the cell binding moiety of RBP would act as a targeting molecule directed to a cancer cell, a similar experiment as Example 2 was carried out using human fibrosarcoma cell strain HT-1080 cells, and RBP Loop 1 as the test peptide (L1:SEQ ID NO: 3) and a scrambled peptide (scr:AKFQKLEPGDDLNI, SEQ ID NO: 23) as a negative control peptide. The lipoplex comprising each peptide was prepared in a similar manner as Example 1 using 10 mM peptide stock solution in DMSO, and added to wells comprising HT-1080 cells such that the final concentration of the peptide was 7.7 µM and the final concentration of the siRNA was 11.5 µg/ml. Moreover, following primers were used as the primer set against HSP47; for GAPDH, the human/rat common primer set against described in Example 2 was used.

```
Human HSP47:
(forward primer, SEQ ID NO: 24)
5' TGACCTGCAGAAACACCTGG 3'

(reverse primer, SEQ ID NO: 25)
5' AGGAAGATGAAGGGGTGGTC 3'
```

From the result shown in FIG. 6, it is understood that the peptide of the cell binding moiety of RBP would act as a targeting molecule directed to a cancer cell in a similar manner as vitamin A. Because it has been known that vitamin A acts as the targeting molecule directed to various cancer cells (see, Patent Literature 2), this result indicates that the peptides and peptide mimetics described in Examples 1-4 would also act as the targeting molecule directed to various cancer cells.

The results of Examples 1-6 also suggest that the targeting molecule of the present invention has a similar targetability as vitamin A, etc. described in Patent Literatures 1-9 and Non-Patent Literature 1 and can be successfully applied to the uses described in these references such as, for example, the treatment, detection, imaging and diagnosis of fibrosis and neoplastic diseases of various organs, and the labeling, detection and imaging of cells such as a stellate cell, a myofibroblast, a cancer-associated fibroblast and a tumor cell.

A skilled person would understand that a number of various alteration can be made without departing from the spirit of the present invention. Therefore, it should be understood that the embodiments of the present invention described herein are merely of illustration and not intended to limit the scope of the present invention.

The invention claimed is:

1. A targeting carrier comprising a targeting molecule and a carrier component, wherein the targeting molecule is present in an amount effective to deliver the carrier and a substance to a target cell selected from the group consisting of a stellate cell, a myofibroblast, a cancer-associated fibroblast, a tumor cell and a stimulated by retinoic acid 6 (STRA6)-expressing cell, wherein the targeting molecule is 10-50 amino acids long, wherein the targeting molecule consists of an amino acid sequence selected from the group consisting of SEQ ID NOS: 3, 4, 6-13, 20-21 and 22, and wherein the carrier component is a lipid.

2. A composition comprising the targeting carrier according to claim 1.

* * * * *

UNITED STATES PATENT AND TRADEMARK OFFICE
CERTIFICATE OF CORRECTION

PATENT NO. : 9,976,142 B2
APPLICATION NO. : 15/301258
DATED : May 22, 2018
INVENTOR(S) : Kenjiro Minomi It is certified that error appears in the above-identified patent and that said Letters Patent is hereby corrected as shown below:

On the Title Page

In Column 1 (Notice) at Line 3, After "0 days." delete "days.".

In Column 2 (Item (56)) at Line 40, Under Other Publications, change "[$^3$ H]" to --[$^3$H]--.

In the Specification

In Column 1 at Line 15 (Approx.), Below "like." insert --REFERENCE TO SEQUENCE LISTING--, as a new heading.

In Column 1 at Line 18 (Approx.), Change "12" to --8--.

In Column 8 at Line 58, After "invention" insert --.--.

In Column 13 at Lines 1-2, Change "N,N',N",N"-tetramethyl-N,N',N",N"-" to --N,N',N",N'''-tetramethyl-N,N',N",N'''- --.

In Column 20 at Line 6, Change "alkylene, —O—O(O)—C$_{1-4}$ alkylene," to -- —O—C$_{1-4}$ alkylene, —O—C(O)—C$_{1-4}$ alkylene,--.

In Column 32 at Line 61, Change "andirbesartan." to --and irbesartan.--.

In Column 34 at Line 3, Change "al-" to --α1- --.

In Column 34 at Line 55, Change "Cy™2," to --Cy™ 2,--.

In Column 35 at Line 30, Change "ethylendiamine," to --ethylenediamine,--.

Signed and Sealed this
Fourth Day of September, 2018

Andrei Iancu
*Director of the United States Patent and Trademark Office*

CERTIFICATE OF CORRECTION (continued)
U.S. Pat. No. 9,976,142 B2

In Column 44 at Line 47, Before "diagnosing" delete "for".

In Column 44 at Line 55, Before "diagnosing" delete "for".